US009289420B2

(12) United States Patent  
Gil et al.

(10) Patent No.: US 9,289,420 B2
(45) Date of Patent: *Mar. 22, 2016

(54) METHOD OF ACTIVATING REGULATORY T CELLS WITH ALPHA-2B ADRENERGIC RECEPTOR AGONISTS

(71) Applicant: Allergan, Inc., Irvine, CA (US)

(72) Inventors: Daniel W. Gil, Corona Del Mar, CA (US); John E. Donello, Dana Point, CA (US); Veena Viswanath, Irvine, CA (US); Lauren M. B. Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 14/070,956

(22) Filed: Nov. 4, 2013

(65) Prior Publication Data

US 2014/0066483 A1    Mar. 6, 2014

Related U.S. Application Data

(62) Division of application No. 13/207,801, filed on Aug. 11, 2011, now Pat. No. 8,575,207.

(60) Provisional application No. 61/374,124, filed on Aug. 16, 2010.

(51) Int. Cl.
| A61K 31/4439 | (2006.01) |
| A61K 31/17 | (2006.01) |
| A61K 31/4164 | (2006.01) |
| A61K 31/4168 | (2006.01) |
| A61K 31/4178 | (2006.01) |
| A61K 31/421 | (2006.01) |

(52) U.S. Cl.
CPC ............. *A61K 31/4439* (2013.01); *A61K 31/17* (2013.01); *A61K 31/4164* (2013.01); *A61K 31/4168* (2013.01); *A61K 31/4178* (2013.01); *A61K 31/421* (2013.01)

(58) Field of Classification Search
CPC .............. A61K 31/17; A61K 31/4164; A61K 31/4178; A61K 31/421; A61K 31/4168
USPC .......... 514/396, 401, 340, 377, 397, 398, 587
See application file for complete search history.

(56) References Cited

U.S. PATENT DOCUMENTS

| 4,166,452 A | 9/1979 | Generales |
| 4,256,108 A | 3/1981 | Theeuwes |
| 4,265,874 A | 5/1981 | Bonsen |
| 6,040,292 A * | 3/2000 | Sommer ................ A61K 38/30 424/10.1 |
| 6,329,369 B1 | 12/2001 | Chow |
| 6,534,542 B2 | 3/2003 | Chow |
| 6,545,182 B2 | 4/2003 | Chow |
| 6,787,517 B1 | 9/2004 | Gil |
| 6,841,684 B2 | 1/2005 | Chow |
| 7,091,232 B2 | 8/2006 | Chow |
| 7,345,065 B2 | 3/2008 | Gil |
| 7,858,653 B2 * | 12/2010 | Galley ................ C07D 233/88 514/398 |
| 2003/0092766 A1 | 5/2003 | Chow |
| 2004/0132824 A1 | 7/2004 | Gil |
| 2004/0220402 A1 | 11/2004 | Chow |
| 2005/0075366 A1 | 4/2005 | Heidelbaugh |
| 2005/0267186 A1 | 12/2005 | Chow |
| 2009/0306161 A1 | 12/2009 | Fang et al. |

FOREIGN PATENT DOCUMENTS

| WO | WO01/78702 A2 | 10/2001 |
| WO | WO01/78703 A2 | 10/2001 |
| WO | WO02/076950 A2 | 10/2002 |
| WO | WO03/099289 A2 | 12/2003 |
| WO | WO2009/020578 A1 | 2/2009 |
| WO | WO2009/091760 A1 | 7/2009 |
| WO | WO2009/091874 A1 | 7/2009 |
| WO | 2009152052 A1 | 12/2009 |
| WO | WO2011/014332 A1 | 2/2011 |

OTHER PUBLICATIONS

Bao, Jingyin et al., Expression of α2-adrenoreceptor in T lymphocytes, Journal of Nantong University (Medical Sciences), 2005, vol. 25, Issue 5, pp. 319-320 and 323 [Abstract—English Translation].
International Search Report dated Oct. 21, 2011 for PCT/US2011/047426—filed Aug. 11, 2011.
U.S. Appl. No. 11/172,229, filed Jun. 29, 2005, Chow.
U.S. Appl. No. 11/232,323, filed Sep. 20, 2005, Heidelbaugh.
U.S. Appl. No. 11/232,341, filed Sep. 20, 2005, Heidelbaugh.
U.S. Appl. No. 60/613,870, filed Sep. 28, 2004, Heidelbaugh.
U.S. Appl. No. 60/695,650, filed Jun. 29, 2005, Chow.
U.S. Appl. No. 60/747,444, filed May 17, 2006, Chow.
U.S. Appl. No. 60/884,718, filed Jan. 12, 2007, Heidelbaugh.
U.S. Appl. No. 60/917,828, filed May 14, 2007, Heidelbaugh.
U.S. Appl. No. 60/911,422, filed Apr. 13, 2007, Ripperger.
U.S. Appl. No. 60/911,478, filed Apr. 12, 2007, Chow.
U.S. Appl. No. 60/948,389, filed Jul. 6, 2007, Fang.
Asano, Masanao; et al.: Autoimmune Disease as a Consequence of Developmental Abnormality of a T Cell Subpopulation, J. Exp. Med. 184:387-396 (1996).
Baecher-Allan, Clare; et al.: $CD4^+CD25^{high}$ Regulatory Cells in Human Peripheral Blood[1], J. Immunol. 167(3):1245-1253 (2001).
Bluestone, Jeffrey; et al.: Natural Versus Adaptive Regulatory T Cells, Nature Rev. Immunol., 3:253 (2003).
Bonomo, Adriana; et al.: Pathogenesis of Post-Thymectomy Autoimmunity, J. Immunol. 154:6602-6611 (1995).
Conklin, Bruce; et al.: Substitution of Three Amino Acids Switches Receptor Specificity of $G_q\alpha$ to That of $G_1\alpha$, Nature 363;274-6 (1993).

(Continued)

*Primary Examiner* — Jennifer M Kim
(74) *Attorney, Agent, or Firm* — Barbara C. Potts

(57) ABSTRACT

Disclosed herein is a method of upregulating regulatory T-cells, and treating diseases that would benefit from such upregulation, by administering an alpha-2 receptor agonist.

8 Claims, 12 Drawing Sheets

(56) References Cited

OTHER PUBLICATIONS

Dixon, F.J.; et al.: Inhibition of T Cell Proliferation and Sle-Like Syndrome of MRL/1 Mice by Whole Body or Total Lymphoid Irradiation[1,2], J. Immunol., vol. 125, No. 5, 2137-2142 (1980).
Friese, Manuel; et al.: Humanized Mouse Models for Organ-Specific Autoimmune Diseases, Current Opinion in Immunology 18, 704-709 (2006).
Greene, T.W., et al: Protective Groups in Organic Synthesis, Wiley, New York, $2^{nd}$ edition (1991).
Hu, P., McLachlan E.M.: Macrophage and Lymphocyte Invasion of Dorsal Root Ganglia After Peripheral Nerve Lesions in the Rat. Neuroscience 112:23-38 (2002).
Kingsley, Cherry; et al.: $CD25^+CD4^+$ Regulatory T Cells Prevent Graft Rejection: CTLA-4- and IL-10-Dependent Immunoregulation of Alloresponses[1], J. Immunol. 168:1080 (2002).
Messier, Terri; et al.: High Throughput Assays of Cloned Adrenergic, Muscarinic, Neurokinin, and Neurotrophin Receptors in Living Mammalian Cells, Pharmacol. Toxicol. 76:308-311 (1995).
Moalem Gila; et al.: Immune and Inflammatory Mechanisms in Neuropathic Pain, Brain Res Rev 51, 240-264 (2006).
Moalem G.; et al.: T Lymphocytes Play a Role in Neuropathic Pain Following Peripheral Nerve Injury in Rats. Neuroscience 129, pp. 767-777 (2004).
Nakamura, Kazuhiko; et al.: Cell Contact-Dependent Immunosuppression by $CD^+CD25^+$Regulatory T Cells is Mediated by Cell Surface-Bound Transforming Growth Factor-β, J. Exp. Med. 194:629-644 (2001).
Neve, Kim; et al.: Dopamine D2 Receptor Stimulation of $Na^+/H^+$ Exchange Assessed by Quantification of Extracellular Acidification, J. Biol. Chem. 267:25748-25753 (1992).
Read, Simon; et al.: Cytotoxic T Lymphocyte-Associated Antigen 4 Plays an Essential Role in the Function of $CD25^+CD4^+$ Regulatory Cells That Control Intestinal Inflammation, J. Exp. Med. 192:295-302 (2000).
Remington's Pharmaceutical Sciences, Mack Publishing Company, Easton, Pa., 16th Edition, 1980.
Riley, James; et al.: Human T Regulatory Cell Therapy: Take a Billion or So and Call Me in the Morning. Immunity, 30(5), 656-665, (2009).
Romero-Sandoval, Alfonso; et al.: Clonidine Reduces Hypersensitivity and Alters the Balance Between Pro-and Anti-Inflammatory Leukocytes After Local Injection at the Site of Inflammatory Neuritis. Brain Beh. Immun. 21; 569-580, (2007).
Sakaguchi, Shimon; et al.: Immunologic Tolerance Maintained by $CD25^+CD4^+$ Regulatory T Cells: Their Common Role in Controlling Autoimmunity, Tumor Immunity, and Transplantation Tolerance, Immunol. Rev. 182:18-32 (2001).
Salomon, Benoit; et al.: B7/CD28 Costimulation is Essential for the Homeostasis of $CD4^+ CD25^+$Immunoregulatory T Cells That Control Autoimmune Diabetes, Immunity 12:431-440 (2000).
Stephens, Leigh; et al.: Human $CD4^+CD25^+$ Thymocytes and Peripheral T Cells Have Immune Suppressive Activity In Vitro, Eur. J. Immunol. 31:1247-1254 (2001).
Shevach, Ethan: $CD^+CD25^+$ Suppressor T Cells; More Questions Than Answers, Nature Rev. Immunol. 2:389-400 (2002).
Shevach, Ethan: Regulatory T Cells in Autoimmunity. Annu. Rev. Immunol. 18:423-449 (2000).
Shimizu, H.; et al.: A Radioisotopic Method for Measuring the Formation of Adenosine 3',5'-Cyclic Monophosphate in Incubated Slices of Brain, J. Neurochem. 16:1609-1619 (1969).
Small, Steven; et al.: Immunosuppression-Induced Leukoencephalopathy From Tacrolimus (FK506). Ann Neurol 40:575-580 (1996).
Spengler R.N.; et al.: Stimulation of Alpha-Adrenergic Receptor Augments the Production of Macrophage-Derived Tumor Necrosis Factor. J Immunol 145: 1430-1434 (1990).
Suri-Payer, E.; et al.: Pathogenesis of Post-Thymectomy Autoimmune Gastritis. Identification of Anti-H/K Adenosine Triphosphatase-Reactive T Cells, J. Immunol. 157(4):1799-1805 (1996).
Taams, Leonie; et al.: Human Anergic/Suppressive $CD4^+ CD25^+$ T Cells: A Highly Differentiated and Apoptosis-Prone Population. Eur. J. Immunol. 31:1122-1131 (2001).
Takahashi, Takeshi; et al.: Immunologic Self-Tolerance Maintained by $CD25^+ CD4^+$ Naturally Anergic and Suppressive T Cells: Induction of Autoimmune Disease by Breaking Their Anergic/Suppressive State, Int. Immunol. 10:1969-1980 (1998).
Tang, Qizhi; et al.: The $Foxp^+$ Regulatory T Cell: a Jack of All Trades, Master of Regulation. Nature Immunol 9: 239-244 (2008).
Titinchi Sa'ad; et al.: $Alpha_2$-Adrenoreceptors in Human Lymphocytes: Direct Characterization by [$^3$H]-Yohimbine Binding. Biochem Biophys Res Commun 121(1):1-7 (1984).
Thornton, Angel; et al.: $CD4^+ CD25^+$ Immunoregulatory T Cells Suppress Polyclonal T Cell Activation in Vitro by Inhibiting Interleukin 2 Production. J Exp Med 188:287-296 (1998).
Tran, Dat; et al.: Therapeutic Potential of $FOXP3^+$ Regulatory T Cells and Their Interactions With Dendritic Cells. Human Immunol 70: 294-299 (2009).
Willerford, Dennis; et al.: Interleukin-2 Receptor Alpha Chain Regulates the Size and Content of the Peripheral Lymphoid Compartment. Immunity 3(4):521-530 (1995).

\* cited by examiner

FIG. 3
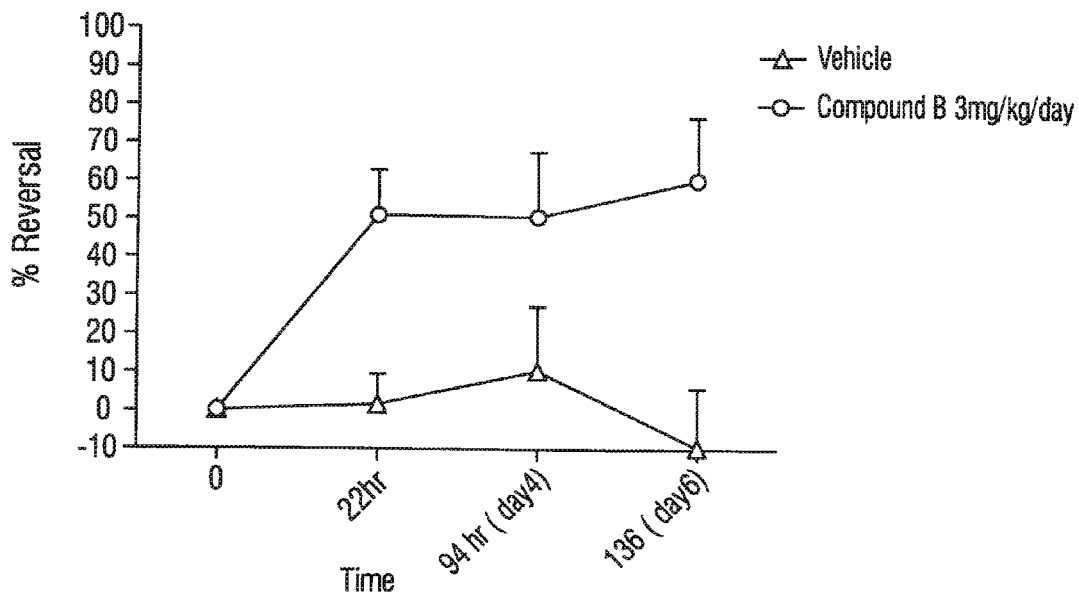
Frequency of CD4+ T cells that are CD25hi (Tregs) within the cervical lymph nodes
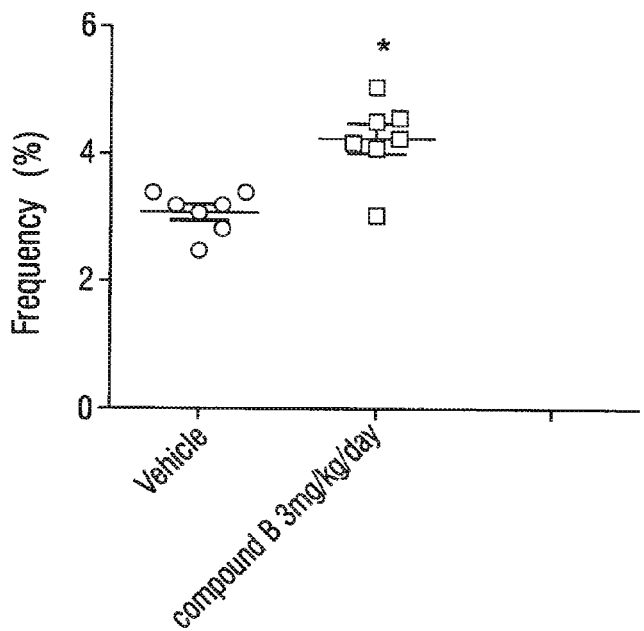
*p<0.01 compared to vehicle, one-way ANOVA with Bonferoni's post-test

FIG. 4
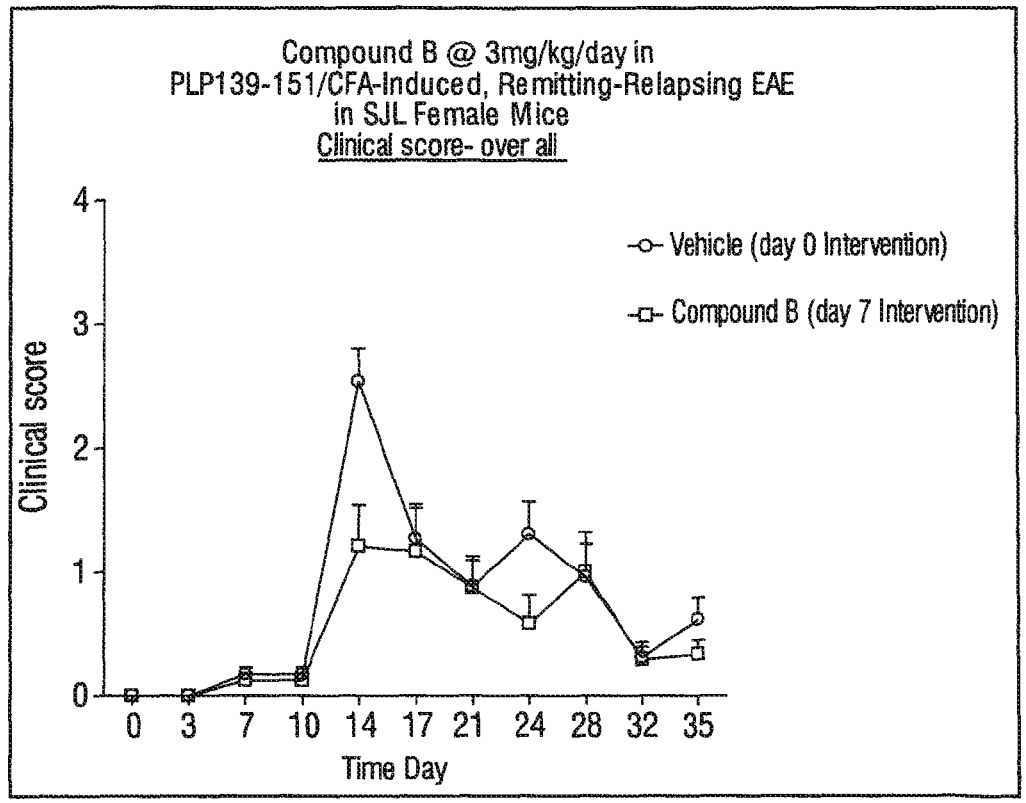
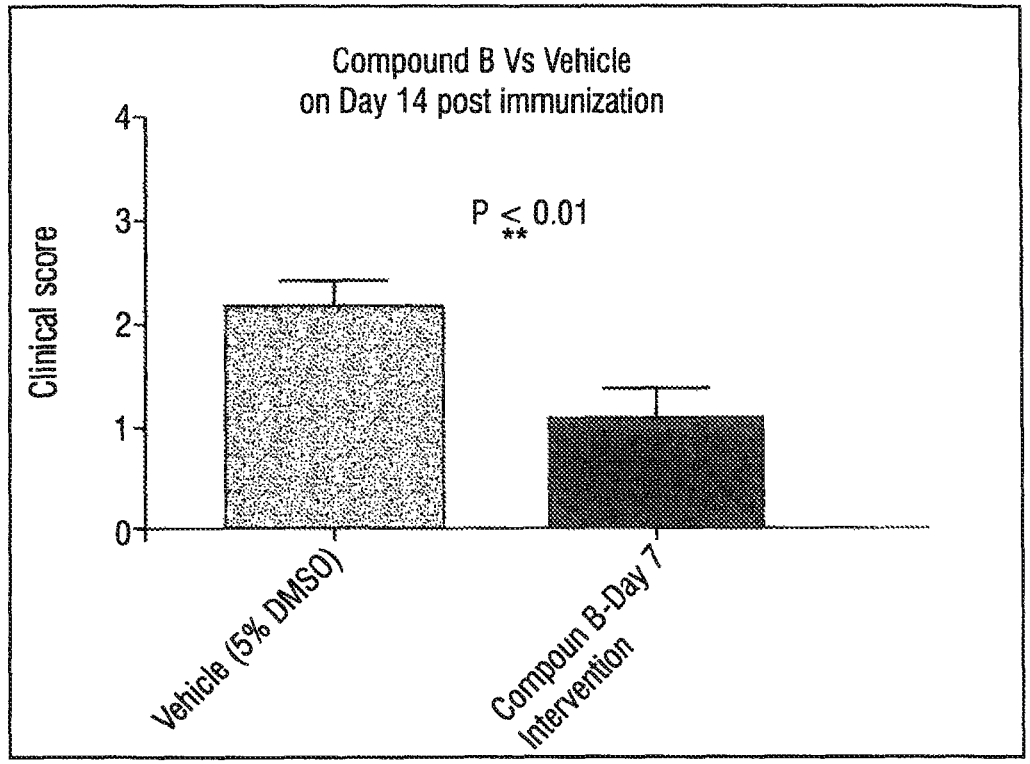

FIG. 10
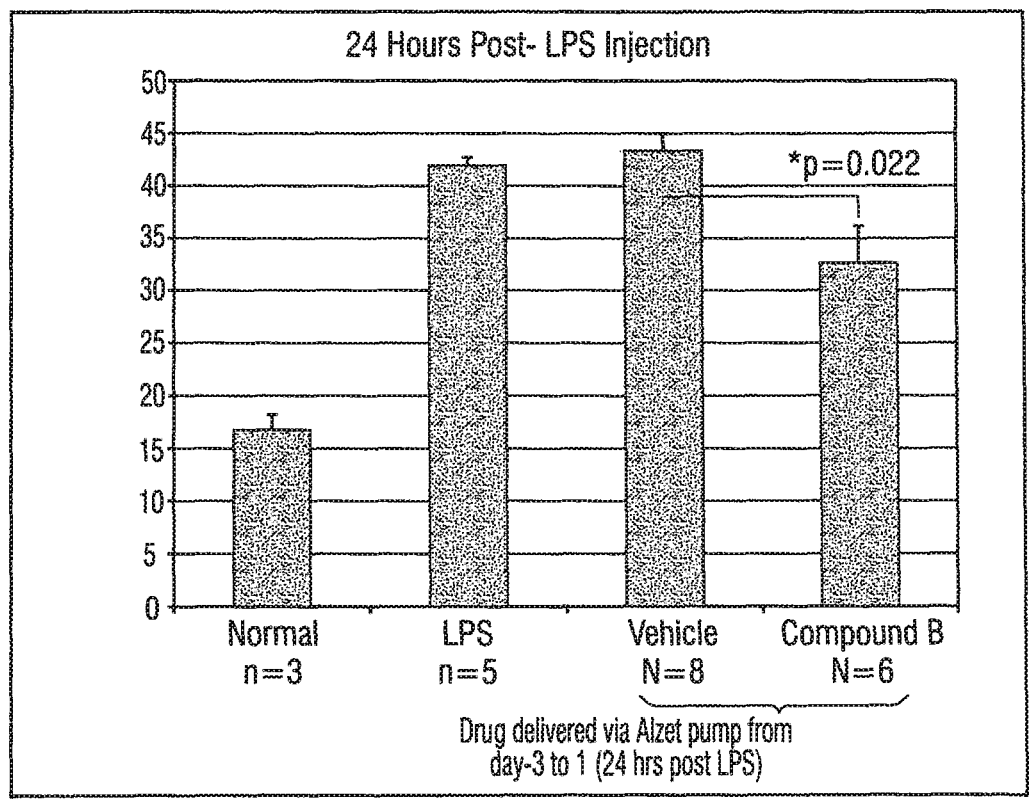
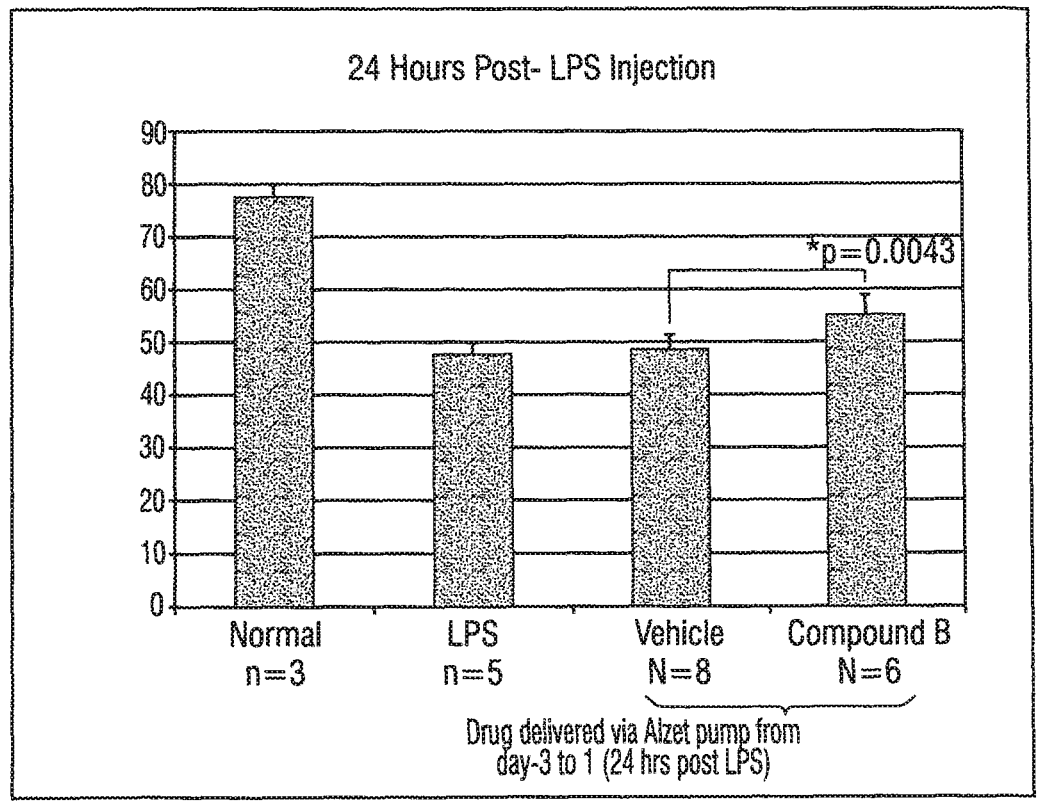

METHOD OF ACTIVATING REGULATORY T CELLS WITH ALPHA-2B ADRENERGIC RECEPTOR AGONISTS

CROSS-REFERENCE TO RELATED APPLICATION

This application is a divisional of U.S. application Ser. No. 13/207,801, filed Aug. 11, 2011, which claims the benefit of U.S. Provisional Patent Application Ser. No. 61/374,124, filed Aug. 16, 2010, both of which are incorporated herein by reference in their entirety.

BACKGROUND

Disclosed herein is the discovery that there are alpha-2B adrenergic receptors on a subtype of T cells, and that alpha-2 receptor agonists may be used to modulate the activity of such T cells and thereby treat those diseases in which T cell dysfunction plays a role, including neuritis, Guillan-Barre syndrome, rheumatoid arthritis, type I diabetes, multiple sclerosis (MS), graft-versus-host disease (GVHD), autoimmune uveitis, ocular inflammation, keratoconjunctivitis sicca (dry eye syndrome), sjogren's syndrome, atopic dermatitis, psoriasis, inflammatory bowel disease, irritable bowel syndrome, asthma, and aplastic anemia.

BRIEF SUMMARY OF THE INVENTION

The present invention provides a method of upregulating regulatory T cell function in a patient, the method comprising administering to a patient needing such upregulation an alpha-2B receptor agonist.

In another embodiment, the present invention provides a method of upregulating regulatory T cell function in a patient, the method comprising administering to a patient needing such upregulation an alpha-2 receptor agonist lacking significant alpha-2A receptor agonist activity.

In another embodiment, the regulatory T cell referred to in the preceding two paragraphs is a CD25+, FoxP3+ T cell.

In another embodiment, the present invention provides a method of treating a disease selected from neuritis, Guillan-Barre syndrome, rheumatoid arthritis, type I diabetes, multiple sclerosis, graft-versus-host disease, autoimmune uveitis, ocular inflammation, dry eye disease, atopic dermatitis, psoriasis, inflammatory bowel disease, asthma, and aplastic anemia by administering to a patient in need of such treatment an alpha-2B receptor agonist.

In another embodiment, the present invention provides a method of treating a disease selected from neuritis, Guillan-Barre syndrome, rheumatoid arthritis, type I diabetes, multiple sclerosis, graft-versus-host disease, autoimmune uveitis, ocular inflammation, dry eye disease, atopic dermatitis, psoriasis, inflammatory bowel disease, asthma, and aplastic anemia by administering to a patient in need of such treatment an alpha-2 receptor agonist lacking significant alpha-2A receptor agonist activity.

In another embodiment, the alpha-2 receptor antagonist of the present invention is administered for an initial period, and then administered again for a second period after a withdrawal period has elapsed.

In another embodiment, the alpha-2 receptor antagonist of the present invention is administered for an initial period, and then administered again for a second period after a withdrawal period has elapsed, wherein the initial, second, and withdrawal periods are one, two, three, four, five, six, seven, eight, nine, ten, eleven, twelve, thirteen, or fourteen days, or one, two, three, or four weeks.

In another embodiment, the alpha-2 receptor antagonist of the present invention is selected from the group consisting of:

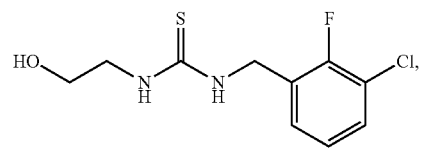

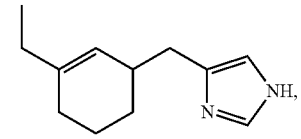

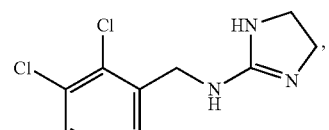

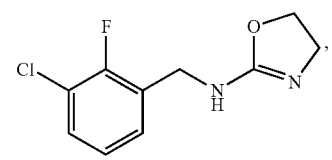

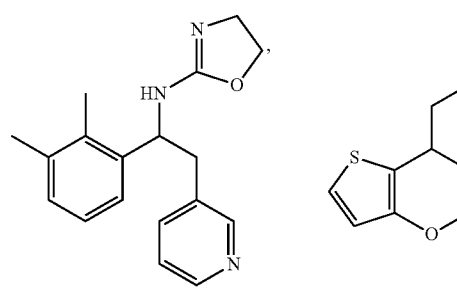

and

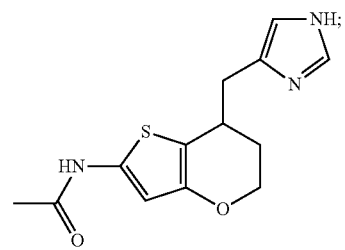

or a pharmaceutically acceptable salt thereof.

In another embodiment, the alpha-2 agonist is selected from the group consisting of thiourea, imidazole, imidazoline, oxazole and oxazoline; or a pharmaceutically acceptable salt thereof.

In another embodiment, the alpha-2 agonist is selected from the group consisting of thiourea, imidazole, imidazoline, and oxazoline; or a pharmaceutically acceptable salt thereof.

In another embodiment, the alpha-2 agonist thiourea is a compound of the formula

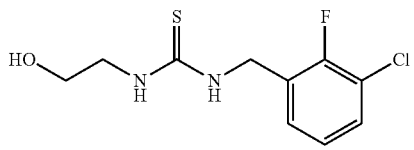 [SMILES: OCCNC(=S)NCc1cccc(Cl)c1F]

or a pharmaceutically acceptable salt thereof.

In another embodiment, the alpha-2-agonist imidazoline is a compound of the formula

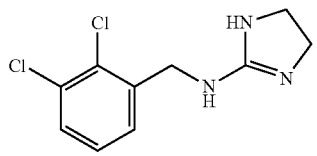 [SMILES: Clc1cccc(CNC2=NCCN2)c1Cl]

or a pharmaceutically acceptable salt thereof.

In another embodiment, the alpha-2-agonist imidazole is a compound selected from the group consisting of:

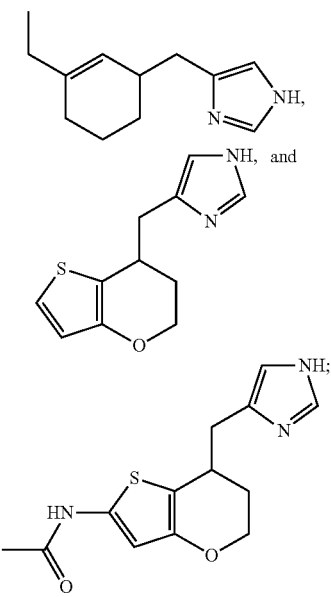

or a pharmaceutically acceptable salt thereof.

In another embodiment, the alpha-2-agonist oxazoline is a compound of the formula

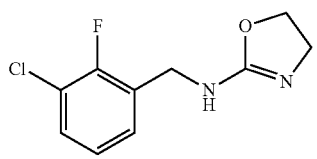 [SMILES: Fc1c(Cl)cccc1CNC1=NCCO1]

or a pharmaceutically acceptable salt thereof.

In another embodiment, the alpha-2-agonist of the present invention is a compound of Formula I

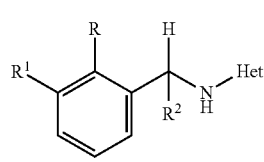

Formula I or a pharmaceutically acceptable salt thereof, wherein:
R and $R^1$ are independently halogen or alkyl;
$R^2$ is H or alkyl which may be unsubstituted or substituted with a heteroaryl or aryl; and
Het is a heterocyclyl group selected from the group consisting of imidazolinyl and oxazolinyl.

In another embodiment, in Formula I:
R and $R^1$ are independently halogen or methyl; and
$R^2$ alkyl is methyl which is substituted with a heteroaryl that is pyridyl.

BRIEF DESCRIPTION OF THE DRAWINGS

FIG. 3 shows that $\alpha_{2B}$-receptor agonist Compound B is analgesic in established MS pain and shows modulation of Treg cells.

FIG. 4 shows that Compound B has a significant effect on clinical course of disease in proteolipid-induced model of relapsing remitting EAE.

FIG. 10 shows that Compound B normalizes the levels of blood neutrophils and lymphocytes in the rat EIU model.

DETAILED DESCRIPTION OF THE INVENTION

Alpha-2 Receptor Agonists

Figure 1:
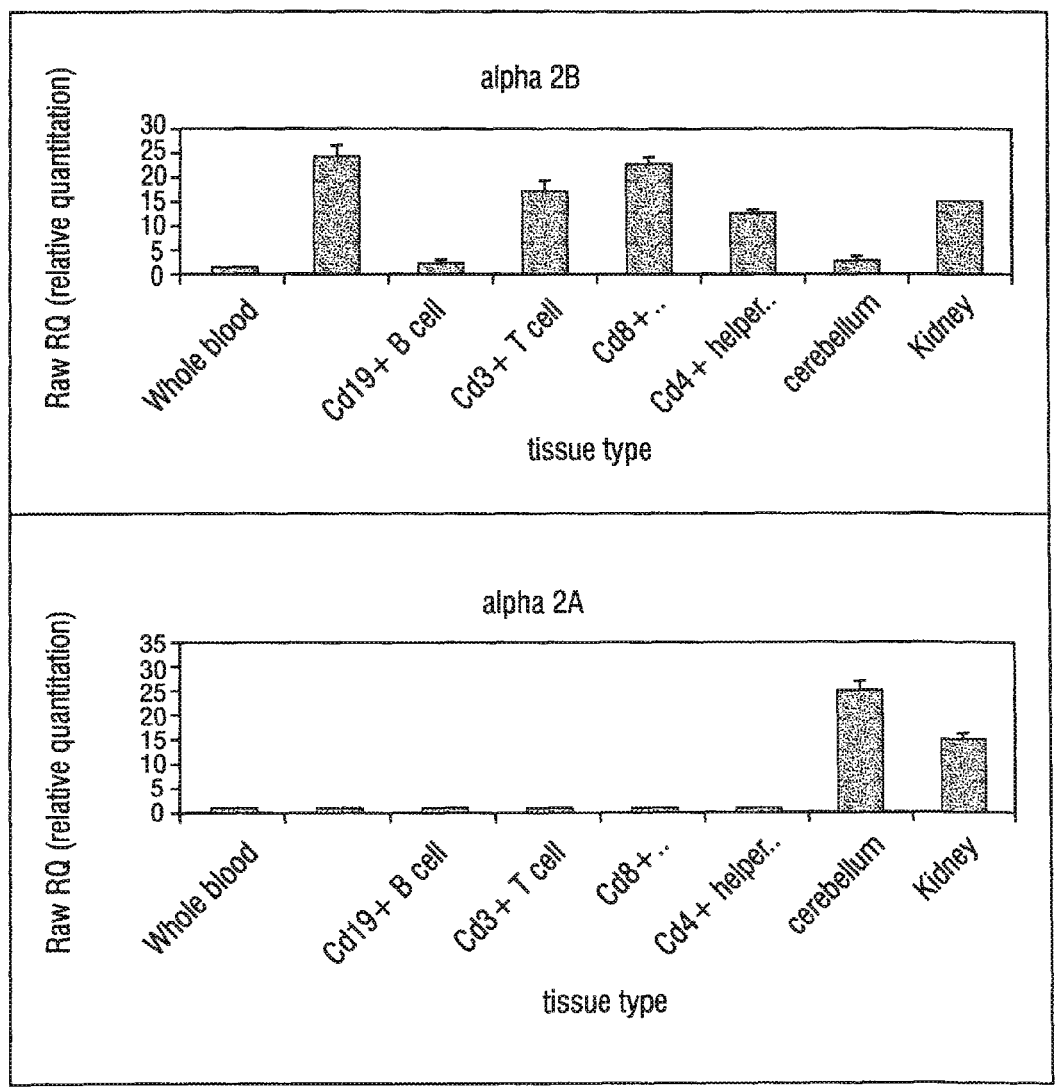
FIG. 1 shows Expression of $\alpha_{2B}$-receptor but not $\alpha_{2A}$-receptor in human T cell subsets via qPCR.

Alpha-2 receptor agonists are those compounds that activate alpha-2 adrenergic receptors. There are three subtypes of this receptor, designated A, B, and C. A compound is an "alpha-2B receptor agonist" if it has greater than 25% efficacy relative to brimonidine at the alpha-2B adrenergic receptor; a compound is an "alpha-2C receptor agonist" if it has greater than 25% efficacy relative to brimonidine at the alpha- 2C adrenergic receptor; and a compound is an "alpha-2B/2C receptor agonist" if it has greater than 25% efficacy relative to brimonidine at both the alpha-2B and alpha-2C adrenergic receptors. The definitions are not mutually exclusive: a compound that is an alpha-2B receptor agonist can also be an alpha-2B/2C receptor agonist; and compound that is an alpha-2C receptor agonist can also be an alpha-2B/2C receptor agonist.

In one embodiment, the methods of the present invention use alpha-2 agonists lacking significant activity at the alpha-2A receptor subtype. An agonist lacks significant alpha-2A receptor activity if the agonist has less than 40% of the efficacy of brimonidine at the alpha-2A receptor subtype. Compounds of the invention include, therefore, alpha-2B receptor agonists; alpha-2B receptor agonists lacking significant alpha-2A activity; alpha-2C receptor agonists; alpha-2C receptor agonists lacking significant alpha-2A activity; alpha 2B/2C receptor agonists; and alpha 2B/2C receptor agonists lacking significant alpha-2A activity. Any of the foregoing compounds may be used, even if they bind receptors other than alpha-2 receptors; for example, alpha-1 receptor agonists may be used, provided that the alpha-1 agonists also have greater than 25% efficacy relative to brimonidine at one or both of the alpha-2B and alpha-2C receptor subtypes, and lack significant alpha-2A receptor activity.

Efficacy, also known as intrinsic activity, is a measure of maximal receptor activation achieved by a compound and can be determined using any accepted assay of alpha-adrenergic receptor activation, such as a cAMP or Receptor Selection and Amplification Technology (RSAT). Efficacy is represented as a ratio or percentage of the maximal effect of the drug to the maximal effect of a standard agonist for each receptor subtype. Brimonidine, itself an alpha-2B receptor agonist (it is has 100% the efficacy of brimonidine at the alpha-2B adrenergic receptor), is used as the standard agonist for the alpha-2B adrenergic receptors.

Agonist activity can be characterized using any of a variety of routine assays, including, for example, Receptor Selection and Amplification Technology (RSAT) assays (Messier et al., *Pharmacol. Toxicol.* 76:308-11 (1995); cyclic AMP assays (Shimizu et al., *J. Neurochem.* 16:1609-1619 (1969)); and cytosensor microphysiometry assays (Neve et al., *J. Biol. Chem.* 267:25748-25753 (1992)). Such assays generally are performed using cells that naturally express only a single alpha-adrenergic receptor subtype, or using transfected cells expressing a single recombinant alpha-adrenergic receptor subtype. The adrenergic receptor can be a human receptor or homolog of a human receptor having a similar pharmacology.

The RSAT assay measures receptor-mediated loss of contact inhibition resulting in selective proliferation of receptor-containing cells in a mixed population of confluent cells. The increase in cell number is assessed with an appropriate detectable marker gene such as beta-galactosidase, if desired, in a high throughput or ultra high throughput assay format. Receptors that activate the G protein, Gq, elicit the proliferative response. Alpha-adrenergic receptors, which normally couple to Gi, activate the RSAT response when coexpressed with a hybrid Gq protein containing a Gi receptor recognition domain, designated Gq/i5. Conklin et al., *Nature* 363:274-6 (1993)).

As an example, an RSAT assay can be performed essentially as follows. NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and protein (1-2 μg). Carrier DNA, for example 40 μg salmon sperm DNA, also can be included to increase transfection efficiency. Fresh media is added on the following day; one to two days later, cells are harvested and frozen in 50 assay aliquots. Transfected cells are thawed, and 100 μl of cells added to 100 μl aliquots of compound to be tested, with various concentrations assayed in triplicate, for example, in 96-well plates. Incubation continues for 72 to 96 hours at 37° C. After washing with phosphate-buffered saline, β-galactosidase activity is determined by adding 200 μl of chromogenic substrate (3.5 mM O-nitrophenyl-β-D-galactopyranoside/0.5% NP-40 in phosphate buffered saline), incubating overnight at 30° C., and measuring optical density at 420 nm. The absorbency is a measure of enzyme activity, which depends on cell number and reflects receptor-mediated cell proliferation. The $EC_{50}$ and maximal effect (i.e., efficacy) of each drug at each receptor is determined.

Alpha-2B and -2C receptor agonists, including those lacking significant alpha-2A receptor activity, are known in the art. Detailed information regarding alpha-2 agonists, including their structure, synthesis, and activity, may be found in U.S. Pat. No. 6,329,369, No. 6,534,542, No. 6,545,182, No. 6,787,517, No. 6,841,684, and No. 7,091,232; in U.S. Patent Application Publication No. 2003/0092766, No. 2004/0132824, No. 2004/0220402, No. 2005/0075366, and No. 2005/0267186; and in U.S. patent application Ser. No. 11/172,229, No. 11/232,323, No. 11/232,341, No. 60/613,870, No. 60/695,650, No. 60/747,444, No. 60/884,718, No. 60/917,828, No. 60/911,422, No. 60/911,478, and No. 60/948,389, the disclosures of all which are incorporated herein by reference.

One can use in the methods of the invention any pharmaceutically acceptable salt, prodrug, isomer, or racemate of any alpha-2 receptor agonist.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, heterocyclyl, heteroaryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl).

Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

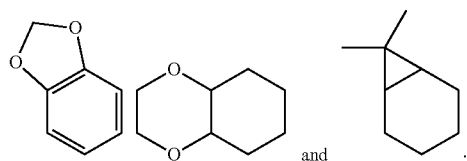

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

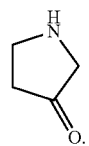

"Heterocyclylalkyl" means a heterocyclyl moiety as defined above linked via an alkyl moiety (defined above) to a parent core. Non-limiting examples of suitable heterocylylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

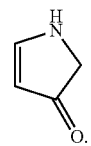

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

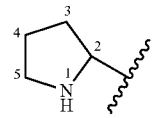

there is no —OH attached directly to carbons marked 2 and 5.

It should also be noted that tautomeric forms such as, for example, the moieties:

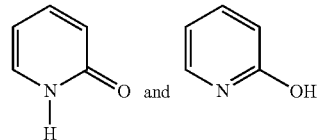 [SMILES: O=c1cccc[nH]1 ; "and" ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Pharmaceutically Acceptable Salts

Alpha-2 receptor agonists may be used as their pharmaceutically acceptable salts.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Prodrugs

One can use in the compositions and methods of the invention a prodrug of any alpha-2 receptor agonist.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e., the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. In this context (definition of "prodrug"), the term "alkyl" has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

The alpha-2 receptor agonists of the invention may be either synthetically produced, or may be produced within the body after administration of a prodrug. Hence, the term "alpha-2 receptor agonist" encompasses both compounds produced by a manufacturing process and those compounds formed in vivo only when another drug administered.

Isomers and Racemates

One can use in the compositions and methods of the invention an enantiomer, stereoisomer, or other isomer of an alpha-2 receptor agonist. One can also use in the compositions and methods of the invention a racemic mixture or one or both racemates, in any proportion.

Dose

The precise dose and frequency of administration depends on the severity and nature of the patient's condition, on the manner of administration, on the potency and pharmacodynamics of the particular compound employed, and on the judgment of the prescribing physician. Determining dose is a routine matter that is well within the capability of someone of ordinary skill in the art. In general, alpha-2 receptor agonists are administered in therapeutically effective doses, that is, at a dose that is sufficient to produce the desired therapeutic effect.

In one embodiment, the compounds of the invention (alpha-2B receptor agonists; alpha-2B receptor agonists lacking significant alpha-2A activity; alpha-2C receptor agonists; alpha-2C receptor agonists lacking significant alpha-2A activity; alpha 2B/2C receptor agonists; and alpha 2B/2C receptor agonists lacking significant alpha-2A activity) provide long-term relief—that is, relief that endures for one or more days after the compounds are withdrawn. Hence, in one embodiment, the method of the invention comprises administering to a patient a compound of the invention for an initial period, then administering the compound again for a second period after a withdrawal period has elapsed. The initial, second, and withdrawal periods may be one, two, three, four, five, six, seven, eight, nine, ten, eleven, twelve, thirteen, or fourteen days, or one, two, three, or four weeks, and may be the same or different. Hence, for example, one can administer a compound of the invention for three days, and then administer the compound again for three days, no sooner than three days after the compound was last administered; or one can administer a compound of the invention for two weeks, and then administer the compound again for one week no sooner than one week after the compound was last administered.

In another embodiment, the initial and second periods are variable and the withdrawal period is fixed. In such embodiments, the initial and second period is at least one, two, three, four, five, six, seven, eight, nine, ten, eleven, twelve, thirteen, or fourteen days, or one, two, three, or four weeks. Hence, for example, one can administer a compound of the invention for at least three days, and then administer the compound again for at least three days no sooner than six days after the compound was last administered; or one can administer a compound of the invention for at least one week, and then administer the compound again for at least a week no sooner than one week after the compound was last administered.

Excipients and Dosage Forms

Those skilled in the art will readily understand that alpha-2 receptor agonists can be admixed with pharmaceutically acceptable excipients which are well known in the art.

A pharmaceutical composition to be administered systemically may be confected as a powder, pill, tablet or the like, or as a solution, emulsion, suspension, aerosol, syrup or elixir suitable for oral or parenteral administration, inhalation or topical administration to the eye or skin.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108, U.S. Pat. No. 4,166,452, and U.S. Pat. No. 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

Activating T Cells

T cells are a class of lymphocytes having specific T cell receptors (TCRs) that are produced as a result of gene rearrangement. T cells have diverse roles, which are accomplished by the differentiation of distinct subsets of T cells, recognizable by discrete patterns of gene expression. Several major T cell subsets are recognized based on receptor expression, such as TCR-$\alpha/\beta$, and TCR$\gamma/\delta$ and invariant natural killer cells. Other T cell subsets are defined by the surface molecules and cytokines secreted therefrom. For example, T helper cells (CD4 cells) secrete cytokines, and help B cells and cytotoxic T cells to survive and carry out effector functions. Cytotoxic T cells (CTLs) are generally CD8 cells, and they are specialized to kill target cells, such as infected cells or tumor cells. Natural killer (NK) cells are related to T cells, but do not have TCRs, and have a shorter lifespan, although they do share some functions with T cells and are able to secrete cytokines and kill some kinds of target cells.

Human and mouse peripheral blood contains a small population of T cell lymphocytes that express the T regulatory phenotype ("Treg"), i.e., positive for both CD4 and CD25 antigens (i.e., those $CD4^+$ T cells that are also distinctly positive for CD25). First characterized in mice, where they constitute 6-10% of lymph node and splenic $CD4^+$ T cell populations, this population of $CD4^+CD25^+$ cells represents approximately only 5-10% of human peripheral blood mononuclear cells (PBMC), or 2-7% of $CD4^+$ T cells, although some donors exhibit a more distinct population of $CD4^+$ and $CD25^+$ cells. About 1-2% of human peripheral blood PBMCs are both CD4 positive ($CD4^+$) and CD25 brightly positive ($CD25^+$) cells.

There are several subsets of Treg cells (Bluestone et al., *Nature Rev. Immunol.*, 3:253 (2003)). One subset of regulatory cells develops in the thymus. Thymic derived Treg cells function by a cytokine-independent mechanism, which involves cell to cell contact (Shevach, *Nature Rev. Immunol.* 2:389 (2002)). They are essential for the induction and maintenance of self-tolerance and for the prevention of autoimmunity (Shevach, *Annu. Rev. Immunol.* 18:423-449 (2000); Stephens et al., 2001; Taams et al., 2001; Thornton et al., 1998; Salomon et al., *Immunity* 12:431-440 (2000); Sakaguchi et al., *Immunol. Rev.* 182:18-32 (2001)). These professional regulatory cells prevent the activation and proliferation of autoreactive T cells that have escaped thymic deletion or recognize extrathymic antigens, thus they are critical for homeostasis and immune regulation, as well as for protecting the host against the development of autoimmunity (Suri-Payer et al., *J. Immunol.* 157:1799-1805 (1996); Asano et al., *J. Exp. Med.* 184:387-396 (1996); Bonomo et al., *J. Immunol.* 154:6602-6611 (1995); Willerford et al., *Immunity* 3:521-530 (1995); Takahashi et al., *Int. Immunol.* 10:1969-1980 (1998); Salomon et al., *Immunity* 12:431-440 (2000); Read et al., *J. Exp. Med.* 192:295-302 (2000). Thus, immune regulatory $CD4^+CD25^+$ T cells are often referred to as "professional suppressor cells."

However, Treg cells can also be generated by the activation of mature, peripheral $CD4^+$ T cells. Studies have indicated that peripherally derived Treg cells mediate their inhibitory activities by producing immunosuppressive cytokines, such as transforming growth factor-beta (TGF-$\beta$) and IL-10 (Kingsley et al., *J. Immunol.* 168:1080 (2002); Nakamura et al., *J. Exp. Med.* 194:629-644 (2001)). After antigen-specific activation, these Treg cells can non-specifically suppress proliferation of either $CD4^+$ or $CD25^+$ T cells (demonstrated by FACS sorting in low dose immobilized anti-CD3 mAb-based co-culture suppressor assays by Baecher-Allan et al., *J. Immunol.* 167(3):1245-1253 (2001)).

Recently, Riley et al. ("Human T regulatory cell therapy: take a billion or so and call me in the morning," Immunity, 30(5), 656-665 (2009)) have shown that regulatory T cells are critical in several pathological conditions involving immune activation (Riley et al., 2009). CD25+, FoxP3+ Tregs have the capacity to block immune responses inflammation and tissue destruction by suppressing the functions of an array of cell types including conventional CD4+ helper T cells, B cell antibody production, CD8+ cytotoxic activity and antigen-presenting cell function and maturation (Tang & Bluestone, 2008). A diminished frequency or dysfunction of Tregs has been reported in many human diseases (Tran & Shevach, 2009).

In one embodiment, the method of the invention comprises administering an alpha-2 agonist to upregulate regulatory T cell function in a patient in whom such upregulation would be beneficial. In another embodiment, the regulatory T cell is a CD25+, FoxP3+ T cell. In another embodiment, the method of the invention comprises administering an alpha-2 agonist to treat diseases such as neuritis, Guillan-Barre syndrome, rheumatoid arthritis, type I diabetes, multiple sclerosis (MS), graft-versus-host disease (GVHD), autoimmune uveitis, ocular inflammation, dry eye disease, atopic dermatitis, psoriasis, inflammatory bowel disease, asthma, and aplastic anemia.

EXAMPLES

The invention is illustrated by the following examples. This is provided for illustration only; many more embodiments are possible.

Evidence for Alpha-2B Action on Regulatory T Cells

The inventors have tested whether $\alpha_{2B}$-selective compounds regulate neuropathic pain states via immune-related mechanisms. Treatment with the $\alpha_{2B}$ agonist, Compound A, attenuated the spinal nerve ligation surgery-induced increase of IL-2 levels (Table 1). IL-2 is a pro-inflammatory cytokine which is essential for regulating T-lymphocyte proliferation. This finding indicates that the $\alpha_{2B}$ agonist effect on acute and chronic allodynia reversal (as described in U.S. Pat. No. 7,345,065, the disclosure of which is incorporated herein by reference) might be mediated via immune cells, particularly T cells. The inventors have also observed expression of $\alpha_{2B}$ receptor, but not $\alpha_{2A}$ receptor, in different subtypes of human T lymphocytes via qPCR. To the inventors' knowledge this is the first demonstration of expression of $\alpha_{2B}$-receptor subtype in T cells (FIG. 1). Additional evidence for the role of immune cells in the persistent pain alleviation mechanisms mediated by $\alpha_{2B}$-receptor agonists was obtained by the fact that the analgesic effect of a second $\alpha_{2B}$ agonist with a different structure, Compound B, was blockable with the immunosuppressant drug FK506 (Table 2). This finding suggests that $\alpha_{2B}$-receptor-induced long-term allodynia reversal requires the presence of activated lymphocytes, since FK506 has been shown to be a potent blocker of T-lymphocyte activation (Small et al, 1996). This finding was confirmed with yet another $\alpha_{2B}$ agonist with a different structure, Compound C, where in FK506 was able to block the long-term analgesic activity of Compound C in the spinal nerve ligation model (Table 3).

Figure 2:
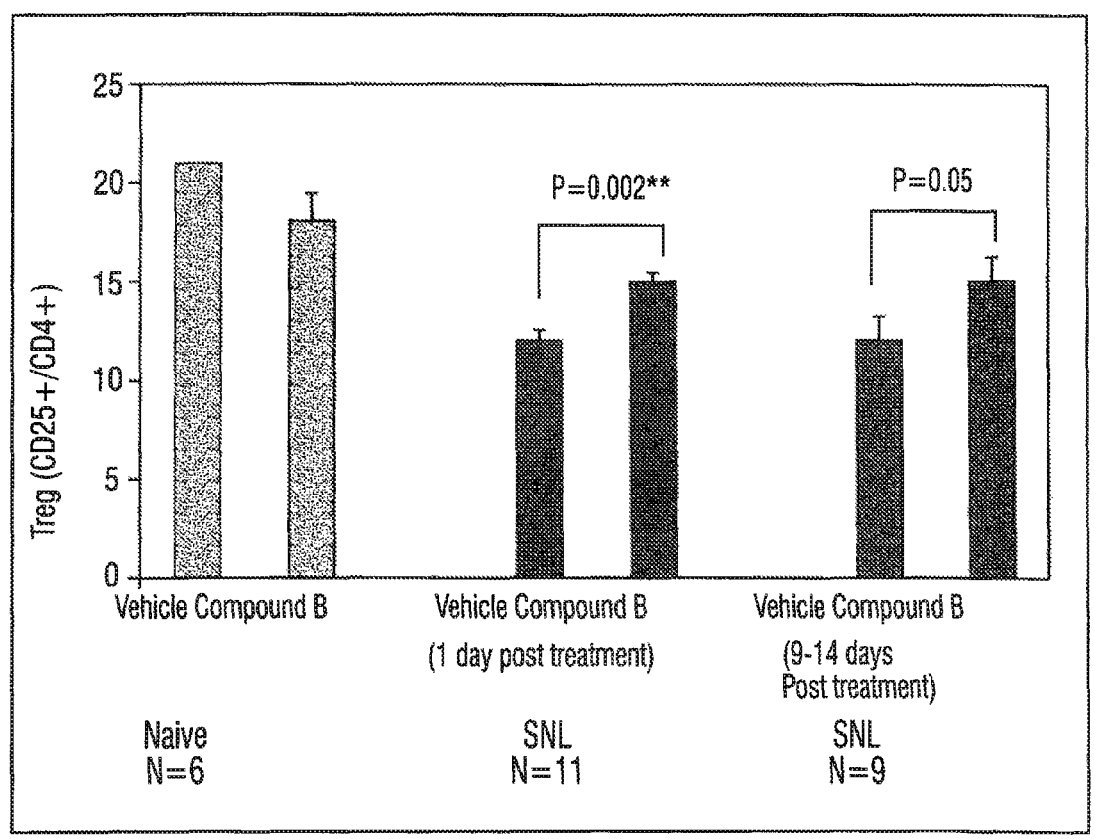
FIG. 2 shows Sustained increase in frequency of spleen CD4+ T cells that are CD4+/CD25+ Treg cells by Compound B in the SNL Rat Model of Allodynic Neuropathic Pain.

Further, the inventors have explored the subtype of T cells involved in $\alpha_{2B}$-receptor-mediated effects and observe a significant and persistent increase in the number of regulatory T Cells (Tregs) in the lymphatic organs in animals with neuropathic pain that have been treated with $\alpha_{2B}$-receptor agonists (FIG. 2). The inventors observed no effect of compound on Treg cell numbers in naïve animals. This suggests that the effect of $\alpha_{2B}$-receptor agonists on Treg cells is dependent on antigen stimulation and there may be antigen-selective expansion of T reg cells.

Effect of Alpha-2B Agonists in a Model of Multiple Sclerosis

The inventors have demonstrated that this mechanism of $\alpha_{2B}$-receptor agonists is generalizable to a second model of pathological T cell activation, a model of multiple sclerosis, and a second species. In mice immunized with proteolipid protein, which causes a relapsing-remitting form of experimental autoimmune encephalomyelitis, Compound B (3 mg/kg/day by osmotic minipump) selectively boosted Treg number and reduced pain [FIG. 3].

TABLE 1

Attenuation of levels of IL-2 in various tissues from SNL rats treated with Compound A (2.4 mg/kg/day via osmotic minipump) or with vehicle

| | Ipsilateral DRGL4 | Ipsilateral DRGL5, L6 | Ipsilateral spinal cord | Serum |
|---|---|---|---|---|
| Naïve | 68 ± 8.5 | 138 ± 0.88 | 397.33 ± 44.58 | 233.33 ± 56.25 |
| SNL rats Vehicle | 139.33 ± 15.76 | 586 ± 7.21 | 523 ± 44.80 | 768.33 ± 271.94 |
| SNL rats Compound A 24 hours | 101.63 ± 20.55 | 211 ± 33.72** | 345 ± 19.34 | 978 ± 77.13 |
| SNL rats Compound A 5 days | 69.52 ± 9.42** | 138.35 ± 22.59** | 351.75 ± 17.19* | 380.25 ± 61.67 |

Data is expressed as mean pg/ml ± standard error of the mean, n = 3-4 in all groups.
Significance values relative to vehicle:
*p < 0.05;
**p < 0.01.

TABLE 2

Pain Reversal by Compound B +/− FK506 in the SNL Rat Model of Allodynic Neuropathic Pain

| Drug Dose in SNL Rats | % Allodynia Reversal | |
|---|---|---|
| (masked) | 24 hr post | 7 day post |
| Vehicle (50% DMSO) | −1.98 ± 6.90 | −7.23 ± 6.22 |
| 3 mg/kg FK506 BID SC | −5.77 ± 3.43 | −6.39 ± 4.85 |
| 1 mg/kg/day Compound B osmotic minipump (treatment for 7 days) | 78.50 ± 7.85 ** | 73.35 ± 11.95 ** |
| 1 mg/kg/day Compound B osmotic minipump + 3 mg/kg FK506 BID SC (Compound B treated for 7 days and FK506 treated for 5 days) | 57.06 ± 14.52* | 16.43 ± 19.42 |

TABLE 3

Pain Reversal by Compound C +/− FK506 in the
SNL Rat Model of Allodynic Neuropathic Pain

| Drug Dose in SNL Rats | % Allodynia Reversal | |
|---|---|---|
| (masked) | 24 hr post | 23 day post |
| Vehicle (50% DMSO) | 0.94 ± 5.65 | 1.72 ± 5.08 |
| 3 mg/kg FK506 BID SC | −0.53 ± 6.21 | 2.01 ± 5.86 |
| 1 mg/kg/day Compound C TID oral for 5 days | 66.06 ± 10.71 ** | 81.48 ± 6.00 ** |
| 1 mg/kg/day Compound C TID oral for 5 days + 3 mg/kg FK506 BID SC for 5 days | 49 ± 13.15* | 21.82 ± 4.26 |

Data are expressed as mean % MPE, which represents the % allodynia reversal from pre-drug baseline, ± standard error of the mean, n = 6 in all groups.
Significance values vs. vehicle:
*p < 0.05;
** p < 0.01.

Table 4, below, shows the structures of Compounds A, B and C:

| COMPOUND | STRUCTURE |
|---|---|
| A | 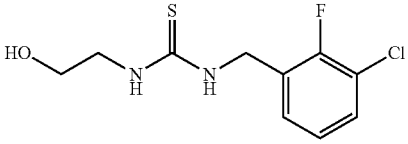 [SMILES: OCCNC(=S)NCc1cccc(Cl)c1F] |
| B | 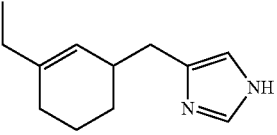 |
| C | 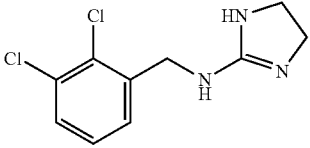 [SMILES: Clc1cccc(CNC2=NCCN2)c1Cl] |

Studies in Other T Cell Mediated Disease Models

Figure 5:
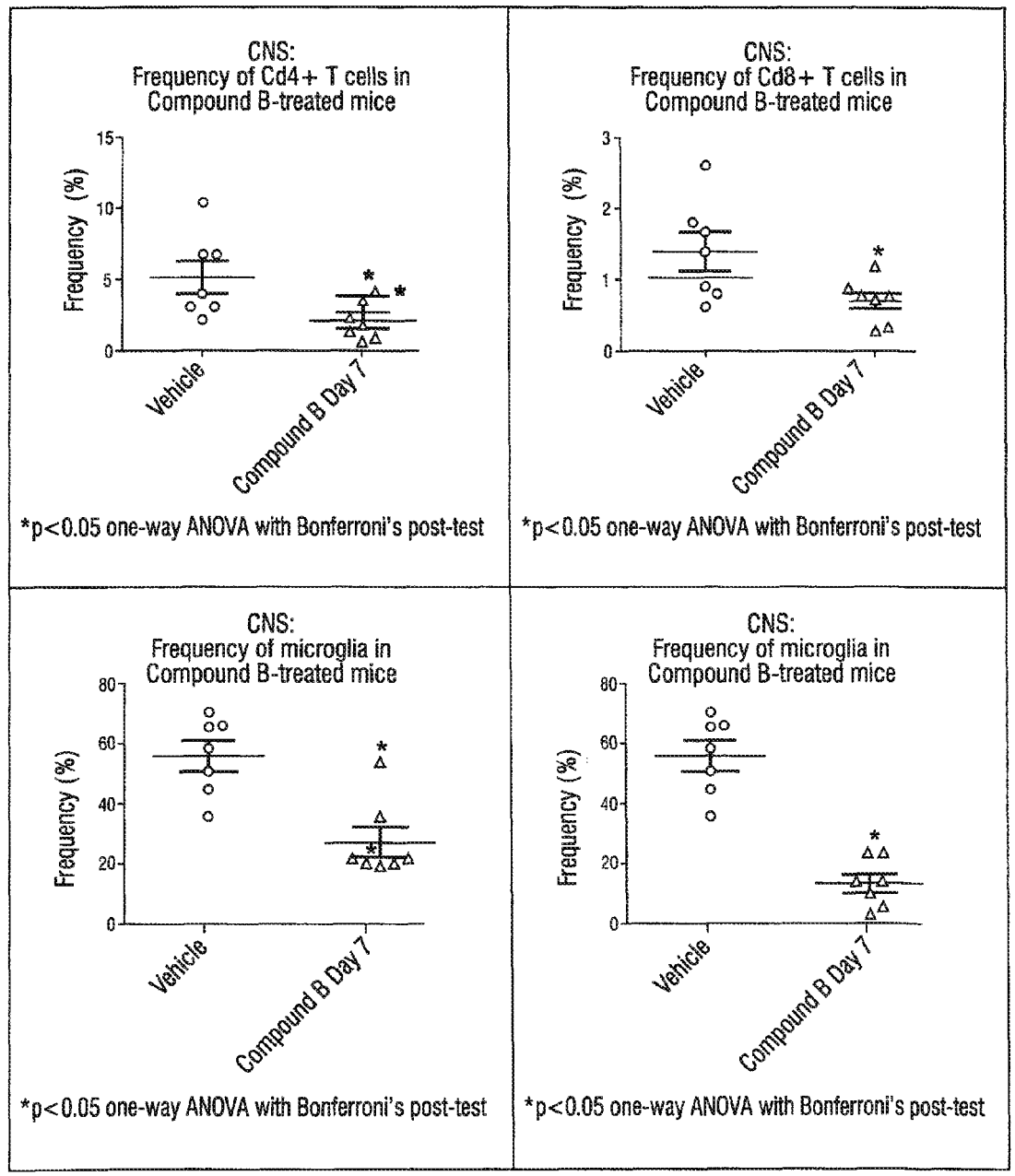
FIG. 5 shows that Compound B significantly reduced the presence of immune cells in the CNS in PLP-induced model of relapsing remitting EAE.
Figure 6:
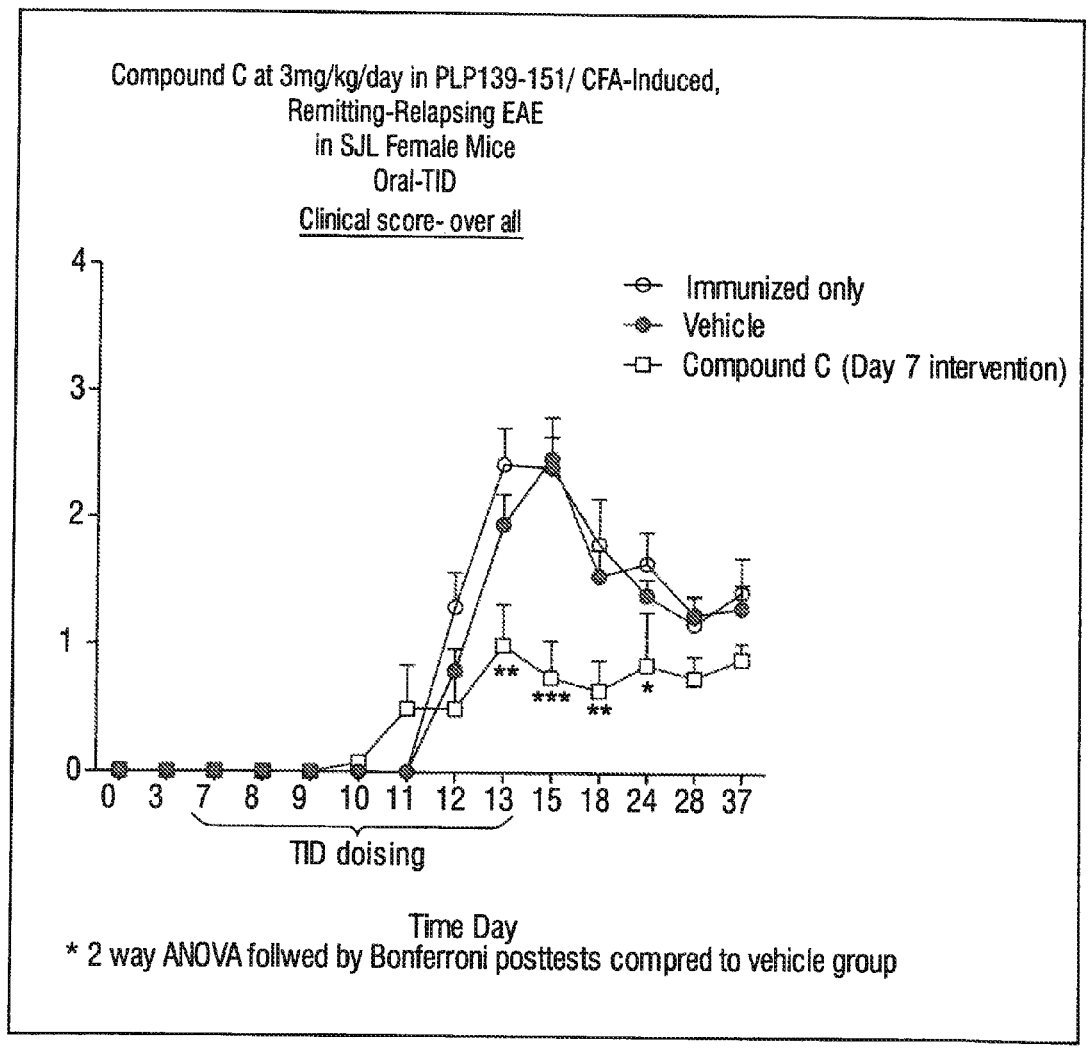
FIG. 6 shows that Compound C has a significant effect on clinical course of disease in proteolipid-induced model of relapsing remitting EAE.
Figure 7:
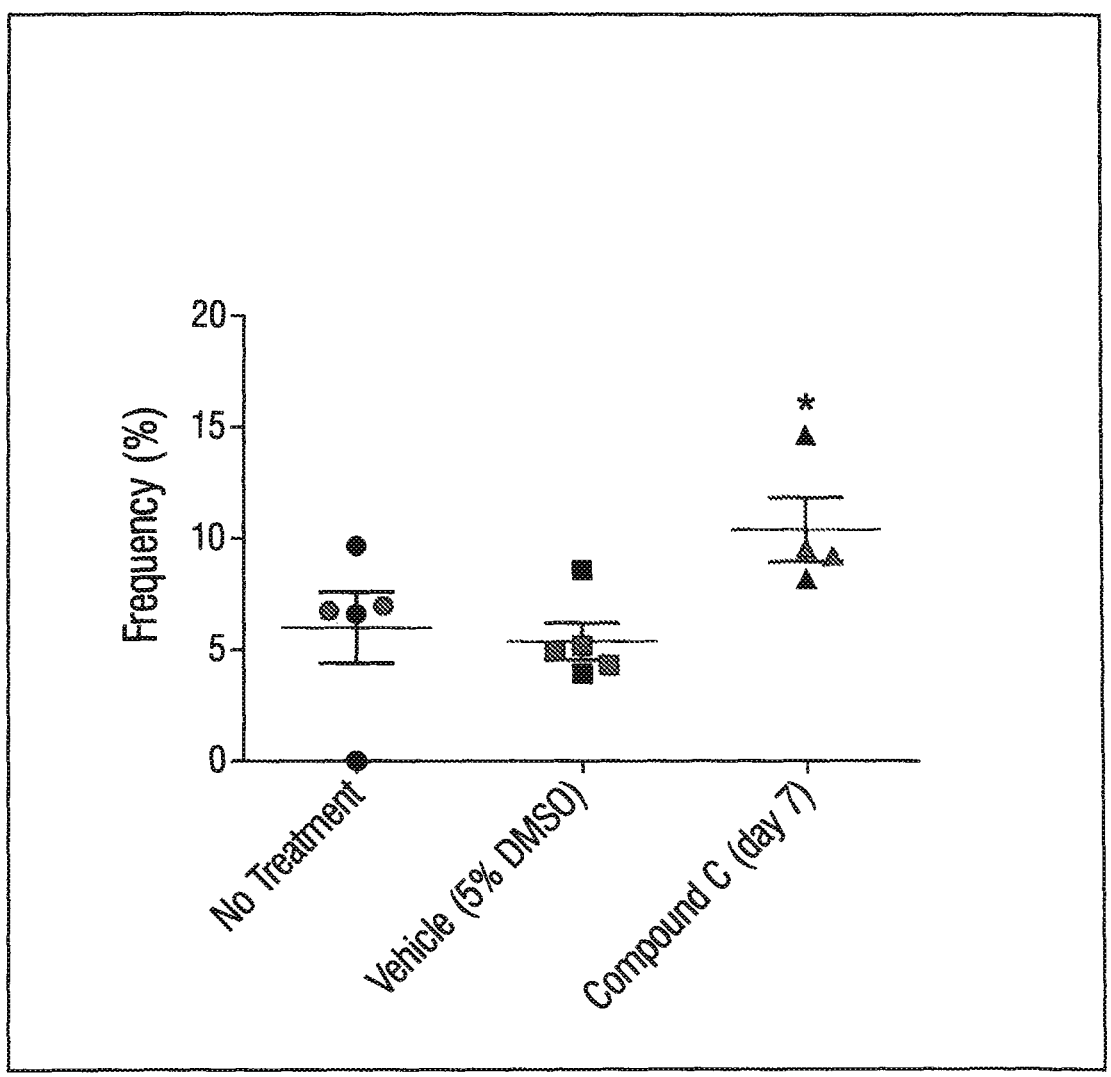
FIG. 7 shows that Compound C significantly increases the frequency of regulatory T cells in the spinal cord in PLP-induced model of relapsing remitting EAE.

Studies of the mechanism of $\alpha_{2B}$-receptor agonists mediated effects in Chung model of neuropathic pain and in MS-induced pain model indicated a significant and persistent increase in the number of putative regulatory T Cells (Tregs) in the lymphatic organs. The inventors explored $\alpha_{2B}$-receptor agonists further in the MS model for effects on clinical course of disease and in autoimmune uveitis, endotoxin-induced uveitis, and Dry eye disease. In mice immunized with proteolipid protein, which causes a relapsing-remitting form of experimental autoimmune encephalomyelitis (EAE), treatment with Compound B during the development of clinical disease has a significant effect on attenuating symptoms of MS (FIG. 4). Treatment from days 7-10 reduced the clinical score during relapses on days 14 (p<0.01) and 24. Similar results are obtained when mice are treated continuously. In EAE, pro-inflammatory CD4+ T cells and other inflammatory cells proliferate in the periphery, infiltrate the central nervous system (CNS) which leads to demyelination characterized by a progressive paralysis. Analysis of immune cell infiltration in the CNS via flow cytometry at the end of the study revealed that treatment with Compound B significantly reduced the presence of immune cells (FIG. 5). This indicates that Compound B prevented presence of pathogenic T cells in the CNS, resulting in attenuated encephalomyelitis. Compound C also showed similar efficacy in EAE. Following TID oral dosing (3 mg/kg/day) from day 7-13, the clinical score was significantly reduced compared to vehicle-treated mice from days 13-24 (FIG. 6). Analysis of immune cells in the CNS via flow cytometry on day 37 revealed that Compound C increased the frequency of regulatory T cells (CD4+ CD25hiFoxP3+) in the spinal cord (FIG. 7). The inventors also performed studies to explore the utility of alpha 2B agonists in models of ocular T cell mediated inflammation. Experimental autoimmune uveitis (EAAU) represents an antigen-specific, T cell-mediated autoimmune response that results in disease in the anterior segment. Compound B, dosed at 1 mg/kg/day from days 1-18 or days 7-18 following EAAU induction (3 days of oral TID dosing followed by dosing via osmotic minipump), was effective in partially abrogating anterior inflammation.

Figure 8:
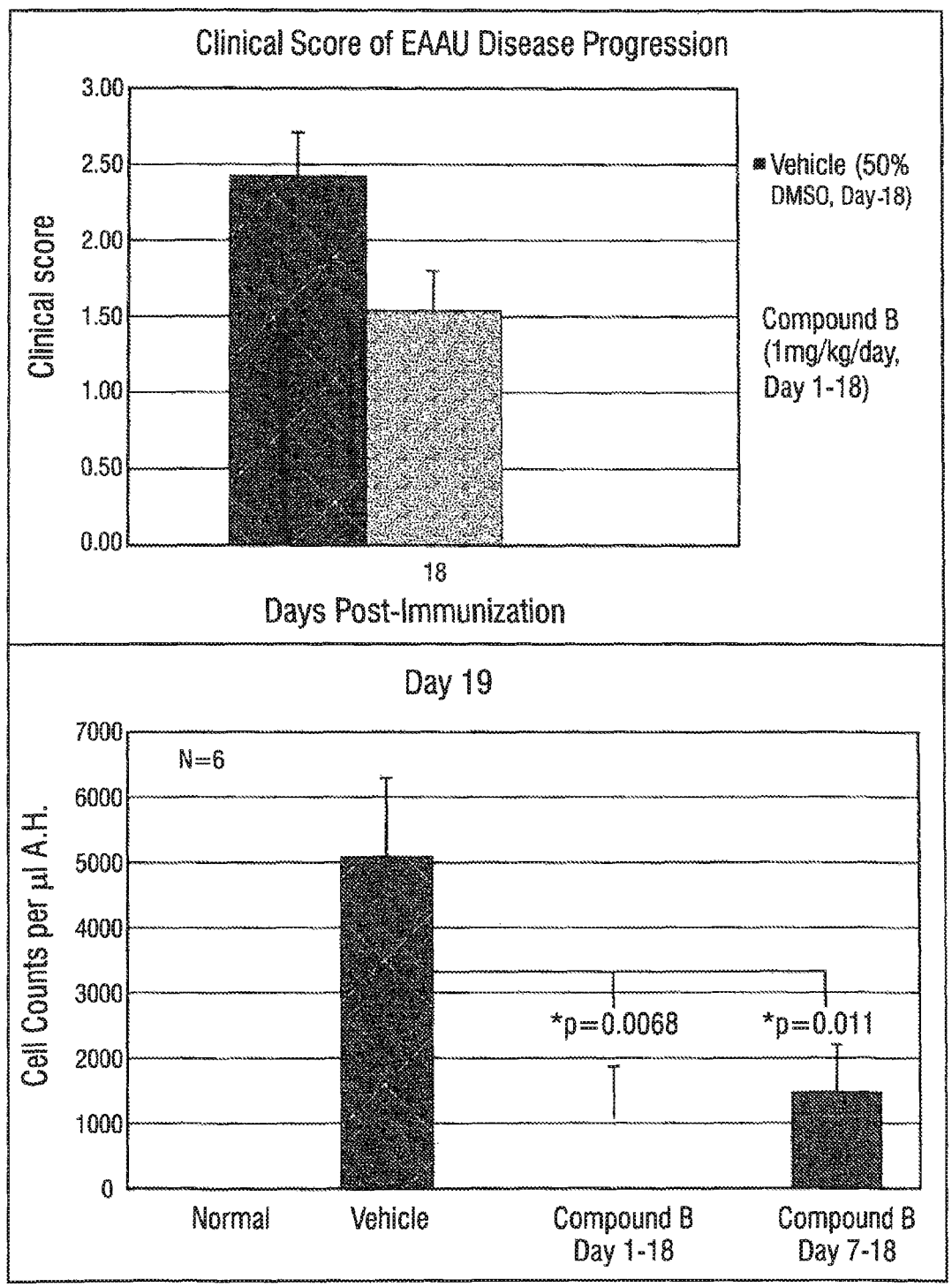
FIG. 8 shows that Compound B has a significant effect on clinical disease and on the number of inflammatory cells in the aqueous humor of EAAU rats.
Figure 9:
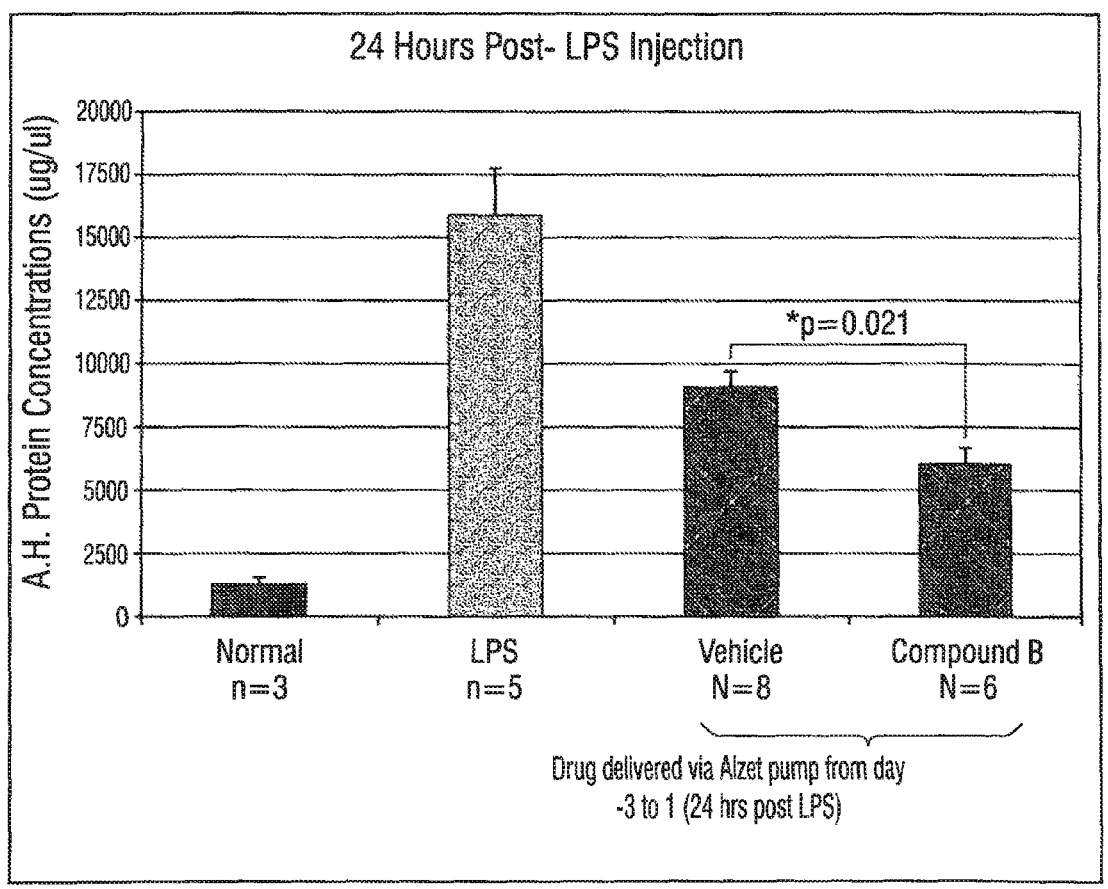
FIG. 9 shows that Compound B has a significant effect on protein concentration in the aqueous humor of EIU rats.
Figure 11:
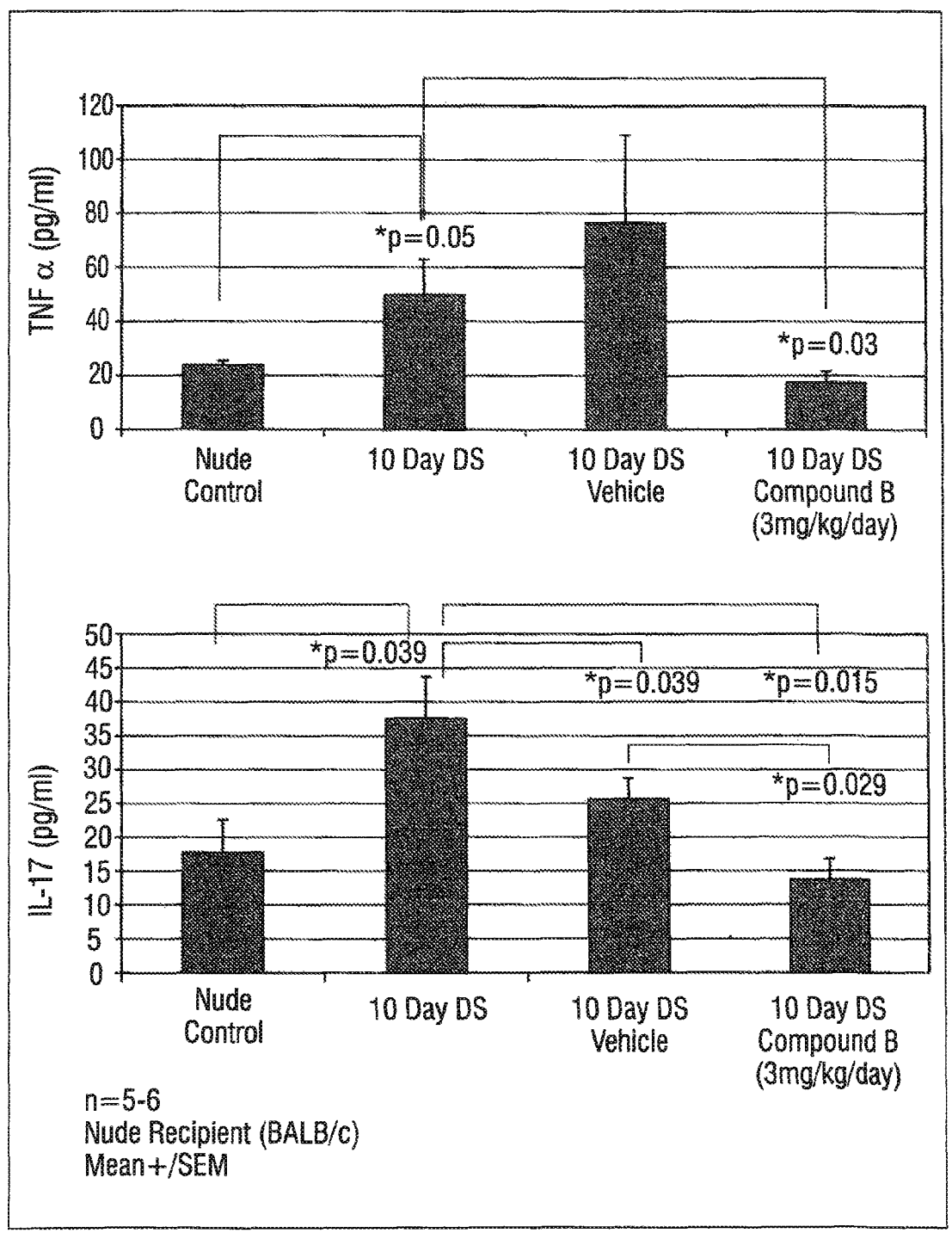
FIG. 11 shows that Treatment of donor with Compound B starting at initiation of desiccating stress significantly reduced recipient tear TNF-alpha and IL17 levels.
Figure 12:
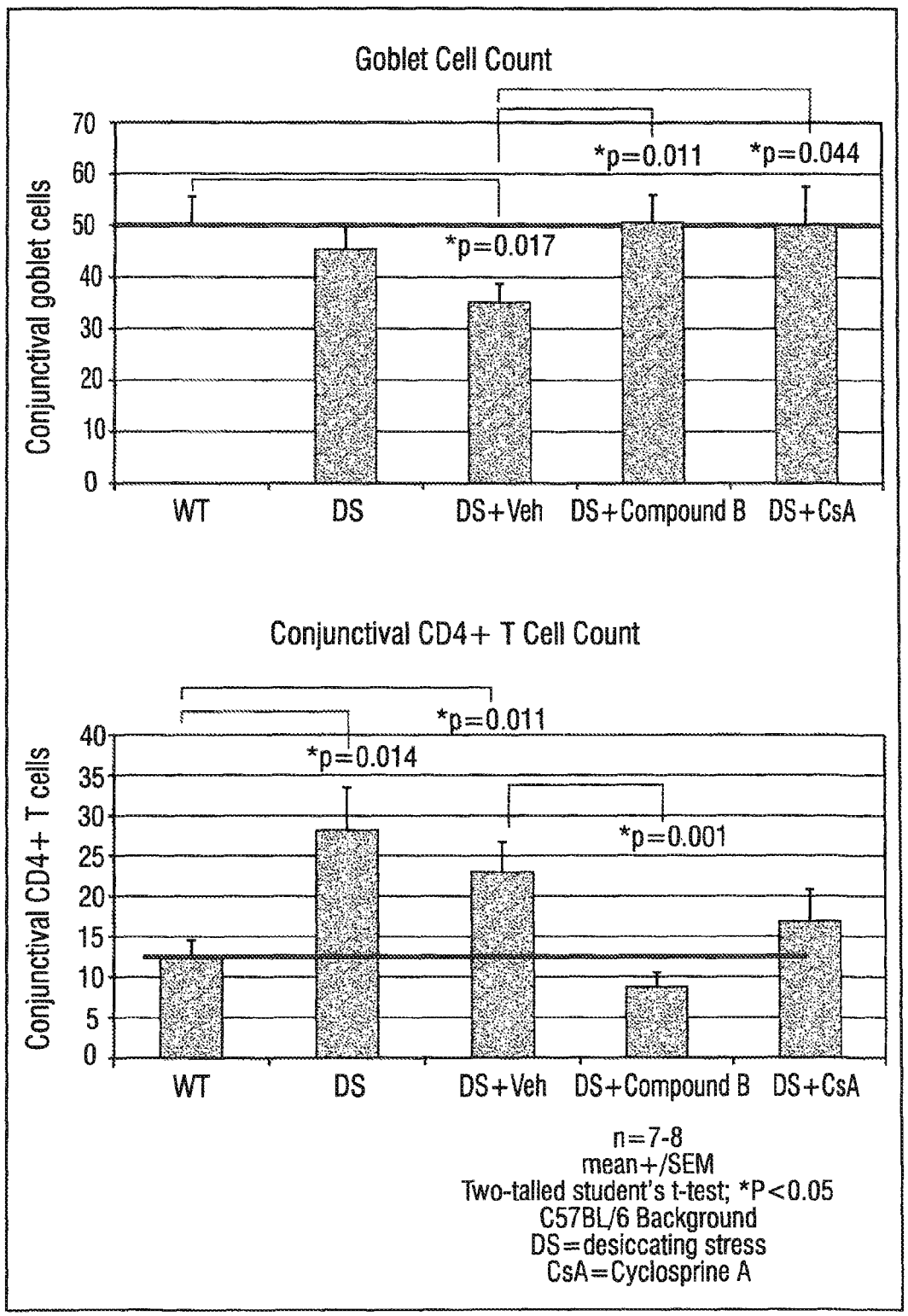
FIG. 12 shows that Treatment with Compound C in a therapeutic mode starting after exposure of mice to desiccating stress significantly reduced goblet cell loss and T cell infiltration into the conjunctiva.

Compound B decreased clinical scores of anterior uveitis and decreased inflammatory cell numbers in the aqueous humor (FIG. 8). In addition, Compound B appeared to be effective in normalizing immune response as seen by decreased neutrophil cell counts in the blood, normalized lymphocyte populations in the blood and normalized CD4+ T cell population in the spleen. A similar effect of Compound B was also observed in the acute endotoxin-induced uveitis (EIU) model. Compound B (1 mg/kg/day delivered by osmotic minipump) significantly inhibited protein exudation in the aqueous humor of EIU rats when compared with untreated or the vehicle-treated (saline) controls (FIG. 9). The increase in blood neutrophils and decrease on blood lymphocyte populations as a result of LPS stimulation was significantly normalized by Compound B but not the vehicle treatment (FIG. 10). An adoptive transfer study in a model of dry eye disease shows that the $\alpha_{2B}$ agonist effect on ocular inflammation involves T cells. Following 10 days of blower-induced desiccating stress in mice treated with 3 mg/kg/day Compound B or vehicle (3 days of oral TID dosing followed by dosing via osmotic minipump), CD4+ T cells were harvested and transferred to syngeneic nude mice. The recipient mice that received T cells from Compound B-treated mice (for 10 days during exposure to the blower) had significantly reduced levels of cytokines IL-17 and TNFα, key cytokines that contribute to dry eye disease (FIG. 11). Compound B was also tested in a therapeutic mode, wherein the treatment (3 mg/kg/day via osmotic minipump) was given to mice that had been exposed to blower previously. In this mode also Compound B significantly prevented the goblet cell loss and the T cell infiltration into the conjunctiva comparable to Cyclosporine A (FIG. 12). These studies support the hypothesis that the mechanism of Compound B, Compound C and other $\alpha_{2B}$ agonists involves immune modulation.

Methods

Spinal Nerve Ligation Model in Rats

The SNL (or Chung) Model in the rat is an accepted standard animal model of neuropathic pain and is thought to mimic the human causalgia condition with respect to symptoms (guarding behavior, mechanical allodynia) and alleviation by pharmacological agents. For instance, morphine does not alleviate the tactile allodynia while Gabapentin (30 mg/kg p.o.) results in a 50% alleviation of allodynia. The SNL Model is performed by tightly ligating the L-5 and L-6 spinal nerves, which produces tactile allodynia or sensitivity to light touch as described (Kim and Chung, 1992). Male sprague-dawley rats (100-120 grams; Charles River, Wilmington, Mass.) were anesthetized through inhalation of an isoflurane/oxygen mix. The surgical site was shaved and prepared with betadine. An incision was made from the thoracic vertebra XIII toward down the sacrum. The muscle was separated from the spinal vertebra (left side) at the L4-S2 levels. The L6 vertebra was located and then the transverse process was carefully removed with a small rongeur to visually identify the L4-L6 spinal nerves. The L5 and L6 spinal nerves was isolated and tightly ligated with 6-0 silk thread. A complete homeostasis was confirmed and then the wound was sutured. The duration of the surgery was approximately 20 minutes. A small amount of antibiotic ointment was applied to the incised area and the animals were transferred to a plastic recovery cage under a regulated heat-temperature lamp. Animals were not given any topical or local anesthetics post-operatively because they will inhibit the development of the pain syndrome, which is the phenomenon to be studied.

The allodynia is quantitated in the animals having received the Chung surgery by stimulation with a series of 8 Von Frey hairs on the mid planter area of the surgical hind paw in the up-down manner as described in the literature (Dixon, 1980). Von Frey hairs are applied in an up-down manner depending on the response until the 50% threshold is established. The Von Frey hairs are applied to the plantar surface of the surgical paw with just enough force to bend them. A positive response is recorded if the paw is sharply withdrawn. Eight VonFrey hairs were used 3.61, 3.84, 4.08, 4.31, 4.56, 4.74, 4.93 and 5.18 yielding a gram force of 0.25-15 grams.

Von Frey Analysis:

$$\% \text{ Allodynia reversal} = \left[\frac{\text{Post drug threshold} - \text{Pre drug threshold}}{15 - \text{Pre drug threshold}}\right] \times 100$$

$$\text{Mean} \pm SEM:$$

$$\text{Mean} = \text{average of allodynia reversals}$$

$$SEM = STDEV/SQ\ ROOT \text{ of } n$$

Testing with compounds is done 2-3 weeks after surgery to establish stable allodynia. In all experimental animals, baseline measurements were taken prior to drug administration and then at 24 hours and 5-23 days post dosing with Alzet osmotic minipump. The investigator was blinded to the identity of the drug groups. The % allodynia reversal is calculated as: [(Postdrug threshold−Predrug threshold)/(15−Predrug threshold)]×100.

Proteolipid-Induced Experimental Autoimmune Encephalomyelitis in Mice

The mouse model of experimental autoimmune encephalomyelitis (EAE) has been used extensively to understand the mechanisms underlying the immunopathogenesis of MS. Mice immunized with myelin proteins, such as Myelin Binding Protein (MBP), Proteo-Lipid Protein (PLP) and Myelin Oligodendrocyte Glycoprotein (MOG) exhibit many similarities to patients with MS (Friese et al., 2006). Components of the immune system including T cells, macrophage, and antibodies are important contributors to myelin destruction in EAE mice. Further, inflammation also gives rise to multifocal regions demyelination culminating in clinical signs of neurologic dysfunction that include loss of tail tone, abnormal gait and partial-to-complete hind-limb paralysis. PLP-induced EAE model offers the ability to simultaneously investigate the pathogenic mechanisms of CNS inflammation and demyelination and MS-associated pain, a multi-targeted concept that we have optimized here at Allergan. Using sterile technique proteolipid protein myelin peptide (PLP) (139-159: CHCLGKWLGHPDKFVGITYAL) is mixed 1:1 with incomplete Freund's adjuvant (IFA) (Final concentration of 2 mg/ml PLP). 8-10 week old Female SJL mice (Taconic) are injected subcutaneously with 100 µl PLP/IFA (200 µg PLP/injection) on both the right and left hind-flank (day 0) using a 26 G needle. Mice immunized using this protocol experience a relapsing-remitting clinical course with episodes of motor impairment interspersed with periods of remission/clinical improvement. Furthermore, these mice display a robust pain phenotype that is most pronounced during periods of clinical remission.

Using this protocol, the onset of PLP-induced EAE in SJL mice occurs at an incidence of (~90-100%) and is generally apparent by ~12 days post-immunization, reaching peak disease by 14-21 days. PLP-EAE mice show physical symptoms of neurologic impairment, progressing from partial loss of tail tonicity to partial-to-complete hind-limb paralysis. Up to 75% of the mice will experience a relapsing-remitting clinical course with periods of remission flanked by episodes of motor impairment (hind-limb weakness and paralysis). Histologically, mice display extensive inflammation within white matter tracts (areas containing myelinated axons) of the brain and spinal cord, progressive infiltration and accumulation of inflammatory cells, demyelination and axonal loss. Mice with severe EAE show extensive cellular infiltrates, widespread foci of demyelination. PLP-immunized mice typically display the most severe clinical disease during the first episode of neurologic impairment (days 14-21). In general, the pain phenotype is most pronounced beginning after remission from the initial demyelinating event and is sustained until the mice are euthanized.

Mice were routinely visually scored for behavioral abnormalities on a scale from 0-5; 0—no abnormality, 1—partial loss of tail tonicity (partial limp tail), 2—loss of tail tonicity and hind-limb weakness 3—unsteady gait and partial hind-limb paralysis, 4—complete hind-limb paralysis and 5—moribund or dead. Scoring was conducted every-other to every-third day starting on day 7 post-immunization until the mice were sacrificed. Allodynia was measured by the Von Frey hairs method as described earlier. At the end of the study spleen, cervical lymph node, spinal cord and brain were collected to perform flow cytometry.

Dry, Desiccating Stress (DS) in Mice

C57BL/6 (C57BL/6NTac) and B6.Cg/NTac-Foxn1nuNE9 were purchased from Taconic, Inc. (Germantown, N.Y.). Mice were used at 6-10 weeks of age. Animal studies approval was obtained from the Allergan Animal Care and Use Committee. All studies adhered to the Association for Research in Vision and Ophthalmology statement for the Use of Animals in Ophthalmic and Vision Research. As described in the literature dry eye was induced by treating mice with subcutaneous injections of scopolamine hydrobromide (0.5 mg/0.2 ml; Sigma-Aldrich, St. Louis, Mo.) three times a day alternating between the left and right flanks (Neiderkorn et al, 2006). Mice were placed in a cage containing perforated plastic screens on each side of the cage to permit airflow from fans (one fan on each side of the cage) for 16 hr/day in a hood (AirClean Systems, Raleigh, N.C.). Room humidity was kept below 40%. Desiccating stress (DS) was induced for 10 consecutive days. Spleens and cervical lymph nodes (CLN) were collected from mice subjected to DS and NS, and one donor-equivalent of either spleen or CLN CD4+ cells was transferred i.p. to syngeneic nude mice. One splenic equivalent of T cells was equal to $5 \times 10^7$ cells. Three days later samples were collected for analysis. For tear collection, 1.5 µL of PBS was placed on each eye, and then 1 µL of tear was collected from both eyes and placed in 8 µL of cytokine assay buffer (Beadlyte; Millipore, Billerica, Mass.). Buffer and tear fluid were collected by capillary action using a 1 μL volume glass capillary tube (Drummond Scientific, Broomhall, Pa.) that was placed in the tear meniscus of the lateral canthus. Samples were frozen at −80° C. until the time of assay. Histological analysis was done by staining Lacrimal gland samples with antibody to CD4 and H&E staining to quantify goblet cells and T cells in the conjunctiva. To test the compounds in a therapeutic mode, the animals were exposed to the desiccating stress for two weeks and then allowed to rest for 7 days in regular housing cages. The animals were then re-exposed to desiccating stress for an additional 7 days to mimic relapsing form of chronic dry eye disease. Drug treatment with Compound B was started 2 days before re-exposure to desiccating stress. In both the studies Compound B was dosed at 3 mg/kg/day. Adoptive transfer, tear cytokine analysis and histological analysis were performed as described above.

Experimental Autoimmune Anterior Uveoretinitis in Rat

Male Lewis rats (180-200 g) were immunized by a single left hind-footpad injection with 150 μg (in 100 μL) of purified MAA complex from bovine eye. MAA proteins were suspended in phosphate-buffered saline (PBS, pH7.2) and emulsified (1:1 v/v) in complete Freund's adjuvant (CFA, VWR Scientific) containing 1 μg/100 μl of Pertussis Toxin (PTx) emulsion mixture. Control animals were injected with PBS emulsified with CFA and PTx.

Assessment of intraocular inflammation was conducted starting day 7 after immunization, Animals were examined every other day between day 7 and 19 post-immunization for clinical signs and symptoms of uveitis using slit lamp microscopy. Aqueous humor was collected to evaluate the number of inflammatory cells and protein levels. Cell counts were done with 10 ul with a hemacytometer under the light microscope. Protein concentration was measured with a Protein assay solution from Bio-Rad, using BSA as the protein standard. Pro-inflammatory cytokine and chemokine levels were measured on Luminex (Biosource-Invitrogen, Carlsbad, Calif.). Blood, spleen, and eyes were harvested on days 11, 14, and 19 to determine blood leukocyte differentiation, splenic T cell activation status via Flow cytometry, as well as histopathology.

Endotoxin-Induced Uveitis in Rats:

Female Lewis rats (180-200 grams) were purchased from Charles River Laboratory. Rats were footpad-injected (hind left side) with either 100 μl of 1 mg/ml LPS (Sigma) solution (in sterile pyrogen-free saline) or 150 μl of sterile pyrogen-free saline. Animals were sacrificed at 24 hours following LPS injection. Aqueous humor was collected and analyzed to determine inflammatory cell counts, levels of cytokines and chemokine concentration as well as total protein concentrations. Blood leukocyte differentiation and histopathology were also determined if required.

Formulations:

Compound A was formulated in 50% DMSO (Sigma, St. Louis, Mo.). This solution was loaded into the osmotic minipumps (Model 1007D, Alzet Corp., Palo Alto, Calif.) set to deliver the drug at a rate of 0.5 ul/hr resulting in a final dose of 2.4 mg/kg/day. The vehicle for these studies is 50% DMSO administered via osmotic minipumps at a rate of 0.5 ul/hr/kg.

Compound B was formulated in 50% DMSO (dimethyl sulfoxide; Sigma, St. Louis, Mo.). This solution was dosed orally TID at a dose of 0.3 or 1 mg/kg. For dosing in the osmotic minipumps (Model 1007D, Alzet Corp., Palo Alto, Calif.) the compound was loaded onto the pumps set to deliver a final dose of either 1 or 3 mg/kg/day. The vehicle for these studies is 50% DMSO.

Compound C was formulated first in 100% DMSO (Sigma, St. Louis, Mo.), then diluted down in 30% DMSO for a 10 mg/ml solution; 15% DMSO for a 3 mg/ml solution and further dilutions were made in water. The compound was dosed orally TID at a dose of either 0.3 or 1 mg/kg for a total daily dose of 1 or 3 mg/kg/day, respectively.

Flow Cytometry

Superficial cervical lymph node cells and spleen cells were obtained by gentle mechanical processing. $CD4^+$ cells were isolated by using a CD4+ isolation column (Miltenyi Biotech, Auburn, Calif.) according to the manufacturer's protocol. The brain and spinal cord were mechanically disaggregated and mononuclear cells of the CNS were isolated using 37.5% Percoll (Sigma-Aldrich).

To determine surface expression of CD4 (Helper T cells), CD8 (killer T cells), CD25 (activated helper T cells and regulatory T cells), CD45 (macrophage and microglial cells) and F4/80 (macrophage and microglial cells) $5\times10^5$ cells/100 μL FACS buffer (PBS, 0.02% sodium azide [Sigma-Aldrich] and 2% bovine serum albumin) were incubated with appropriate antibodies from BD biosciences, Mountain View, Calif. Isotype control antibodies used for each of the antibodies. The cells were washed two times in FACS buffer and resuspended at $5\times10^5$ cells/100 μL buffer. The tubes containing biotin-labeled antibody received 1.5 μL of an accessory staining pigment (Streptavidin PerCP; BD-Pharmingen) and were placed on ice for 20 minutes in the dark. Expression was analyzed (FACSCalibur with CellQuest software; BD Biosciences, Mountain View, Calif.).

Luminex Analysis of Cytokines

The levels of cytokines were measured with a sensitive, fluorescent multiplex immunobead assay (Luminex; Biosource-Invitrogen, Carlsbad, Calif.), 9 plex rat cytokine/chemokine (RCYTO-80K-09) panel from Millipore was used. Cytokine levels in samples were analyzed by using the corresponding Millipore cytokine Beadmate pairs. For the Luminex assay, a 96-well filter plate (Millipore) was pre-wetted with 25 μl of Beadlyte cytokine assay buffer. A vacuum manifold (Millipore, Billerica, Mass.) was used to aspirate the buffer from the wells. 25 μl of sample was placed in each well. The beads (25 μl) were pipetted into the wells. Standard curves for each cytokine were generated in duplicate by placing 25 μl of the appropriate dilution of standards purchased from Millipore. The plate was incubated overnight with gentle shaking in the dark at 4° C. Beads were washed with Beadlyte cytokine assay buffer (Millipore) and wash buffer was eliminated using a vacuum manifold. 25 μl of the appropriate biotin-conjugated secondary antibody (Millipore) was added to each well for 90 minutes at room temperature with gentle shaking. Beads were incubated with Beadlyte streptavidin-phycoerythrin (1:25 dilution in Beadlyte assay buffer) for 30 minutes at room temperature with gentle shaking. Beads were washed, resuspended in 125 μl of Beadlyte buffer, and analyzed by Luminex 100 instrument (Luminex Corporation, Austin, Tex.). The mean fluorescence intensities obtained from 50 beads per cytokine minimum were analyzed using Upstate Beadview software. Standard curves were generated (8 data points including a zero standard run in duplicate) using a four- or five-parametric logistic curve. R-squared values were between 0.99 and 1. Data are expressed in pg/ml or ng/ml values.

What is claimed:

1. A method of treating dry eye disease in a patient in need of such treatment, the method comprising administering to the patient an alpha-2B receptor agonist, wherein the alpha-2B receptor agonist is a compound of Formula I:

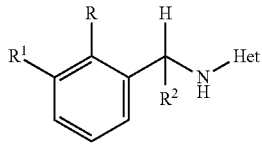

Formula I or a pharmaceutically acceptable salt thereof, wherein:

R and $R^1$ are independently halogen or alkyl;

$R^2$ is H or alkyl which may be unsubstituted or substituted with a heteroaryl or aryl; and Het is imidazolinyl.

2. The method of claim 1, wherein the compound is:

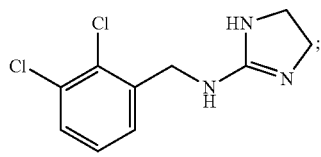 [SMILES: Clc1cccc(CNC2=NCCN2)c1Cl]

or a pharmaceutically acceptable salt thereof.

3. The method of claim 1, wherein the agonist is administered for an initial period, and then administered for a second period after a withdrawal period has elapsed.

4. The method of claim 3, wherein each of the initial, second, and withdrawal periods is independently one, two, three, four, five, six, seven, eight, nine, ten, eleven, twelve, thirteen, or fourteen days, or one, two, three, or four weeks.

5. The method of claim 1, wherein the agonist is administered at a therapeutically effective dose.

6. The method of claim 2, wherein the agonist is administered for an initial period, and then administered for a second period after a withdrawal period has elapsed.

7. The method of claim 6, wherein each of the initial, second, and withdrawal periods is independently one, two, three, four, five, six, seven, eight, nine, ten, eleven, twelve, thirteen, or fourteen days, or one, two, three, or four weeks.

8. The method of claim 2, wherein the agonist is administered at a therapeutically effective dose.

* * * * *